United States Patent
Egyud

[11] Patent Number: 5,849,783
[45] Date of Patent: Dec. 15, 1998

[54] AUTOBIOTICS AND THEIR USE IN ELIMINATING NONSELF CELLS

[75] Inventor: Laszlo G. Egyud, Woods Hole, Mass.

[73] Assignee: Cell Research Corporation, Cambridge, Mass.

[21] Appl. No.: 536,618

[22] Filed: Sep. 28, 1995

Related U.S. Application Data

[63] Continuation of Ser. No. 344,161, Nov. 23, 1994, abandoned, which is a continuation of Ser. No. 24,685, Mar. 1, 1993, abandoned, which is a continuation-in-part of Ser. No. 703,380, May 21, 1991, abandoned, which is a division of Ser. No. 547,983, Jul. 3, 1990, Pat. No. 5,147,652.

[51] Int. Cl.$^6$ .................... A61K 31/40; A61K 31/12; A61K 31/11
[52] U.S. Cl. .................... 514/425; 514/675; 514/693
[58] Field of Search .................... 424/480; 436/829; 514/675, 693, 425

[56] References Cited

U.S. PATENT DOCUMENTS

| | | | |
|---|---|---|---|
| 4,066,650 | 1/1978 | Egyud | 260/281 |
| 4,440,740 | 4/1984 | Fix et al. | 424/1.1 |

FOREIGN PATENT DOCUMENTS

3218121A1   11/1983   Germany.

OTHER PUBLICATIONS

Apple, M.A. and Greenberg, D.M., "Arrest of Cancer in Mice by Therapy with Normal Metabolites," *Cancer Chemotherapy Reports* (*Part 1*) 52(7):687–696 (1968).

Egyud, L.G. and Györgyi, A., "Cancerostatic Action of Methylglyoxal," *Science*, 160:1140 (1968).

Underwood, G.E. et al., "Binding of an Antiviral Agent (Kethoxal) by Various Metabolites," *Proc. Soc. Exp. Biol. Med.*, 100:312–315 (1959).

Underwood, G.E. et al., "Glyoxal and Relatd Compounds as Potential Blood Sterilizing Agents," *Proc. Soc. Exp. Biol. Med.*, 93:421–424 (1956).

Tiffany, B.D. et al., "Antiviral Compounds, I. Aliphatic Glyoxals, α–Hydroxyaldehydes and Related Compounds," *J. Am. Chem. Soc*, 79:1682–1690 (1656).

Nozawa, Y. and Fox, S.W., "Microencapsulation of Methylglyoxal and Two Derivatives," *J. of Pharm. Sci*, 70(4):385–386 (1981).

Thornalley, P.J., "The Glyoxalase System: New Developments Towards Functional Characterization of a Metabolic Pathway Fundamental to Biological Life," *Biochem. J.*, 269:1–11 (1990).

Schenk, P. et al., "Studies on Sucrose–Palmitate–Stearate–Containing Vasicles Encapsulating the Cytostatic Drug Methylglyoxal–Bis–Guanyl–Hydra–zone," *Pharmazie*, 45:747–748 (1990).

Arndt, D. et al., "Liposomes as Carrier of Methyl–GAG," *Oncology*, 44:257–262 (1987).

Taylor, T.W.J. et al., "The Metallic Componds of Certain Monoximes and the Structure of the Oximes," *J. Chem. Soc.*, pp. 2818–2819 (1926).

Jerzykowski, T. et al., "Antineoplastic Action of Methylglyoxal," *Neoplasma*, 17:25–35 (1970).

Schauenstein, H. et al., *Aldehydes in Biological Sustems*, Pion Ltd. London pp. 1–8 (1977).

(List continued on next page.)

*Primary Examiner*—Gollamudi S. Kishore
*Attorney, Agent, or Firm*—Hamilton, Brook, Smith & Reynolds, P.C.

[57] ABSTRACT

Physically and chemically latentiated autobiotics are described. The latentiated autobiotics are useful for the treatment or prevention of any disease or condition, which results from the presence of nonself cells in a vertebrate host. Latentiated autobiotics are furthermore useful in suppressing immune rejection processes, as radiosensitizers and as anticoagulants.

3 Claims, 5 Drawing Sheets

U.S. PATENT DOCUMENTS

Schauenstein, H. et al., "Dicarbonyl Compounds," *Aldehydes in Biological Systems,* Pion Ltd. London pp. 112–157 (1977).

Schauenstein, H. et al., "Schematic Survey of the most Important Aldehydes Involved in Intermediary Metabolism," *Aldehydes in Biological Systems,* Pion Ltd. London pp. 163–171 (1977).

Gordon, S.G., Cancer Procoagulant, in *Hemostatis and Cancer* (ed. L. Muszbek) CRC Press, pp. 19–31 (1987).

Ostro, M.J. and Cullis, P.R., "Use of Liposomes as Injectable–Drug Delivery Systems," *Am. J. Hosp. Pharm.,* 46:1576–1589 (1989).

Rabjohn, J., "Selenium Dioxide Oxidation," *Organic Reactions,* 5:331–387 (1949).

Freedberg, W.B. et al., "Lethal Synthesis of Methylglyoxal by *Escherichia Coli* During Unregulated Glycerol Metabolism," *J. of Bacterial.,* 108(1):137–144 (1971).

Barrett, P.A. et al., "Biological Activities of Some α–dithiosemicarbazones," *Nature,* 206:1340–1341 (1965).

Mehrishi, J.N. and Grassetti, D.R., "Sulphydryl Groups on the Surface of Intact Ehrlich Ascites Tumour Cells, Human Blood Platelets and Lymphocytes," *Nature,* 224:563–564 (1969).

Riley, H.L. et al., "Selenium Dioxide, a New Oxidising Agent. Part 1. Its Reaction With Aldehydes and Ketones," *J. Chem. Soc.* pp. 1875–1883 (1932).

Cox, E.G. et al., "The Planar Configuration of Quadricovalent Compounds of Bivalent Copper and Nickel," *J. Chem. Soc.,* 129:129–133 (1936).

Szoka, F., Jr., "Comparative Properties and Methods of Preparation of Lipid Vesicles (Liposomes)," *Ann. Rev. Biophys. Bioeng.,* 9:467–508 (1980).

Egyud, L.G. and Szent–Györgyi, A., "Cell Division, SH, Ketoaldehydes, and Cancer," *Proc. Acad. Sci USA,* 55:388–393 (1966).

Apple, M.A. and Greenberg, D.M., "Arrest of Cancer in Mice by Therapy with Notmal Metabolites," *Cancer Chem. Rep.,* 51:455–464 (1967).

Stein, S.M. and Berestecky, J.M., "Inhibition of Growth by Masking of Arginine Moieties in Protein at the Cell Surface," *Cancer Research,* 34:3112–3116 (1974).

Stein, S.M. and Berestecky, J.M., "Exposure of an Argenine–Rich Protein at Surface of Cells in S, $G_2$, and M Phases of the Cell Cycle," *J. Cell. Physiol.,* 85:243–249 (1975).

Egyud, L.G., "Studies on Autobiotics: Retine in Human Urine," *Biochem. J.,* 96:19c–20c (1965).

Egyud, l.G., "Studies on Autobiotics: Chemical Nature of Retine," *Proc. Natl. Acad. Sci. USA,* 54(1):200–202 (1965).

Mertz, E.T., "Liposomes Capturing Increases Attention, " *Biotechnology,* 5:6 (1987).

Mehrishi, J.N., "Molecular Aspects of the Mammalian Cell Surface," *Progress in Biophys. and Mol. Biol.,* 125:3–70 (1972).

Ray, M. et al., "Inhibition of Respiration of Tumor Cells by Methylglyoxal and Protection of Inhibition by Lactaldehyde," *Int. J. Caner,* 47:603–609 (1991).

AUTOBIOTICS AND THEIR USE IN ELIMINATING NONSELF CELLS

This application is a continuation of application Ser. No. 08/344,161 filed Nov. 23, 1994 now abandoned, which is continuation of Ser. No. 08/024,685 filed Mar. 1, 1993 abandoned, which is a CIP of Ser. No. 07/703,380 filed May 21, 1991 (now abandoned) which is a divisional application of Ser. No. 07/547,983 filed Jul. 3, 1990 (now U.S. Pat. No. 5,147,652).

BACKGROUND OF THE INVENTION

All vertebrates have an immune system. The essence of the immune system is its capacity to recognize surface features of macromolecules that are not normal constituents of the vertebrate. (Hood, L. E., et al., IMMUNOLOGY, 2d ed., The Benjamin/Cummings Publishing Co., Inc., p.5 (1984)). A properly functioning immune system is able to distinguish "nonself" surface features from "self" surface features, whereby, the immune system selectively destroys and eliminates invading organisms such as bacteria and viruses expressing "nonself" surface features. The immune system also selectively eliminates cells which express "nonself" surface features, such as cancer cells, while accepting cells with "self" surface features.

However, some nonself cells evade the host's immune system by camouflaging their outer surface with host protein. These camouflaged nonself cells remain and proliferate in the host undetected. Undetected nonself cells are the cause of many diseases, which plague man and animals. For example, cells infected with viral diseases (e.g., AIDS, influenza, measles, mumps, chicken pox, shingles, hepatitis) bacterial diseases (e.g., pneumonia, bronchitis, meningitis, carditits, periodontitis, bovine mastitis) fungal diseases (e.g., histoplasmosis, blastomycosis, candidiasis) and parasitic diseases, all result from the infection and proliferation of nonself cells in a host vertebrate.

In addition, malignant cells result when a vertebrate's own cells become nonself. Healthy individuals at any given moment carry about 50,000–100,000 nonself, potentially malignant cells in their body. These nonself cells are generally recognized and killed by the individual's immune system. However, if any of the nonself cells become camouflaged, they will proliferate as malignant cells.

Currently, there are few adequate and specific therapies for most diseases that result from the presence of nonself cells in a host. For example, malignant cells are currently treated either by surgical excision of tumors or by therapies using radiation and highly toxic chemicals. However, surgical excision is not an effective method of treatment when the malignancy has metastasized. In addition, radiation and chemotherapy are nonspecific, often killing normal cells as well as malignant cells.

Another problem is that the cell-kill caused by chemotherapeutic agents follow first-order kinetics. As a result, a constant percentage, rather than a constant number of cells is killed by a given application of a chemotherapeutic agent. To illustrate, if a drug capable of killing 99.99% of malignant cells is administered to a patient, who harbors $10^{12}$ malignant cells, $10^8$ malignant cells would remain. Although the patient would be diagnosed as having a complete clinical remission, any of the $10^8$ malignant cells remaining could cause a relapse in the disease.

Another problem with cancer therapies, as well as therapies for other diseases based on the presence of nonself cells in a host, is that the nonself cells often become resistant to a particular therapeutic agent over time. Attempts to overcome this problem have resulted in protocols using several therapeutic agents concurrently or in rational sequences. Other protocols are aimed at targeting the drugs more specifically to the nonself cells.

A chemotherapeutic agent that could be used to specifically eliminate nonself cells, but not self cells in vivo would be very useful in treating cancer and a variety of other diseases that result from the presence of nonself cells in a host.

Alpha-ketoaldehydes, a series of chemicals containing the alpha-ketoaldehyde radical, are known as potent inhibitors of the proliferation of nonself cells. The antiviral properties of alpha-ketoaldehydes have been intensively and systematically examined and the results published in a series of papers (Underwood, G. E. and S. D. Weed, *Proc. Soc. Exp. Biol. Med.,* 93:421–424 (1956); Tiffany, B. D. et al. *J. Am. Chem. Soc.,* 79:1682 (1957); Underwood, G. E. et al., *Proc. Soc. Exp. Biol. Med.,* 100:312 (1959)). Alpha-ketoaldehydes have also been shown to have a bacteriostatic effect. (Freedberg, W. B. et al. *J. Bacteriol.,* 108:137 (1971); Barrett, P. A., et al. *Nature,* 206:1340 (1965); Egyud, L. G. and A. Szent-Gyorgyi, *Proc. Natl. Acad. Sci., USA,* 55:388–393 (1966)). Recently, alpha-ketoaldehydes have been shown to selectively inhibit respiration of tumor cells. (Ray, M., et al., *Int. J. Cancer,* 47:603–609 (1991); Kisch, B., *Biochem Z,* 253:373, (1932)).

In addition, topical treatment of tumor growth with alpha-ketoaldehydes cures the host (Apple, M. A., and D. M. Greenberg, *Can. Chem. Ther. Rep.,* 51:455–464 (1967); Egyud, L. and A. Szent-Gyorgyi, *Science,* 160:1140 (1968); Jerzykowski, T. et al., *Neoplasma,* 17:25–35 (1970)).

However, alpha-ketoaldehydes are readily metabolized to the corresponding β-hydroxy acids by glyoxalase enzymes, which are present in all living cells, especially red blood cells. Therefore, although free alpha-ketoaldehydes inhibit the proliferation of nonself cells, systemic doses of free alpha-ketoaldehydes have not been successfully used therapeutically due to degradation by metabolic enzymes. When free alpha-ketoaldehydes were used at high concentrations, in an attempt to overwhelm the capacity of the glyoxalase enzyme system, they were found to be toxic.

SUMMARY OF THE INVENTION

The present invention relates to a class of modified chemicals known as latentiated alpha-ketoaldehydes, which can be administered to a vertebrate to specifically eliminate nonself cells, expressing surface features that are not normally expressed on the surface of the vertebrate's cells, while leaving self cells intact.

Latentiated alpha-ketoaldehydes can also be administered to a vertebrate to specifically eliminate invading organisms such as those bacteria, viruses, fungi and parasites which express nonself surface features, as well as the cells infected with these organisms that express nonself surface features (Townsend, A., IMMUNE RECOGNITION AND EVASION: MOLECULAR ASPECTS OF HOST AND PARASITE INTERACTIONS. (1990) Eds. Lex, H. et al. p. 87 Academic Press). Thus, the term "nonself cells", as used herein, will include these vertebrate cells expressing surface features not normally expressed on the vertebrates' cell surface (i.e., altered surface features or surface antigens, such as, but not limited to, tumor cells and fertilized egg cells); cellular organisms such as bacteria, parasites, protozoa, yeasts, molds and including viruses that are able to hide or mask their antigenicity through the use of host protein; and cells which express altered surface features because they are infected with cellular organisms and viruses.

Alpha-ketoaldehydes can be latentiated by chemical means, physical means or both. Unlike free alpha-ketoaldehydes, latentiated alpha-ketoaldehydes retain biological activity much longer in vivo and can be administered in doses that are nontoxic to the host vertebrate.

In one embodiment, the alpha-ketoaldehydes are chemically latentiated by reaction with a secondary amine. In another embodiment, alpha-ketoaldehydes are physically latentiated by entrapment within an encapsulant, such as a liposome. Importantly, chemically latentiated alpha-ketoaldehydes, and physically latentiated, alpha-ketoaldehydes demonstrate the ability to target, or localize at nonself cells. In addition, latentiated alpha-ketoaldehydes are able to target non-self cells with a higher concentration of surface —SH physical group (e.g., malignant cells). Furthermore, because of their small physical size, it is reasonable to predict that latentiated alpha-ketoaldehydes would be able to penetrate the blood/brain barrier and, therefore, can be used to treat diseases resulting from the presence of nonself cells in the brain of a host.

Once localized at the nonself cell, there are several modes by which latentiated alpha-ketoaldehydes cause the destruction of nonself cells in vivo. In one mode, latentiated alpha-ketoaldehydes remove and prevent reformation of the protein coating "camouflaging" the nonself cell. Once the shield is removed, the nonself cell is exposed to foreign cell recognition and destruction by the host's immune system (e.g, natural killer (NK) cells). In another mode, latentiated alpha-ketoaldehydes inhibit protein synthesis and thereby prevent growth and proliferation of the nonself cell. In yet another mode, alpha-ketoaldehydes have been shown to inhibit tumor cell respiration.

An important advantage in the use of alpha-ketoaldehydes for controlling malignancies, or for limiting the proliferation of any nonself cell, is that these chemicals can selectively and directly kill nonself cells. At the same time, they can also enable the host immune system to attack camouflaged nonself cells. By taking away the camouflage, they make these cells vulnerable to the NK cells. As a result, therapy using latentiated alpha-ketoaldehydes provides more than one modality to kill nonself cells. In addition, the use of latentiated alpha-ketoaldehydes as a treatment appears to be resistant to mutations when using methylglyoxal as the alpha-ketoaldehyde being latentiated. This is because methylglyoxal occurs naturally in small quantities inside normal cells. Non-self cells are less likely to develop mutations that will make them resistant to this naturally present material. Thus one can expect that latentiated alpha-ketoaldehydes will be effective in inhibiting and killing those non-self cells (e.g., bacteria, viruses, malignant cells) that are able to develop drug resistance to other pharmaceuticals.

Latentiated alpha-ketoaldehydes are also useful as radiosensitizers and may be useful as diagnostic agents when combined with appropriate radioisotopes or fluorescent agents. In addition, latentiated alpha-ketoaldehydes can be administered to suppress the immune rejection processes of tissue transplantation (e.g., skin grafting, transplantation of pancreatic islet beta-cells, and bone marrow transplants), as an anticoagulant, as a prophylactic agent to prevent pregnancy or blood clots, and as an inhibitor of sulfhydryl enzymes, such as tissue transglutaminase (protein-glutamine gamma-glutanayltransferase). When applied topically to damaged tissue due to burns, wounds, or cuts, the latentiated alpha-ketoaldehydes may act to suppress the growth of bacteria, fungi or other pathogens which may facilitate healing of the damaged tissue.

DETAILED DESCRIPTION OF THE INVENTION

Figure 1A:
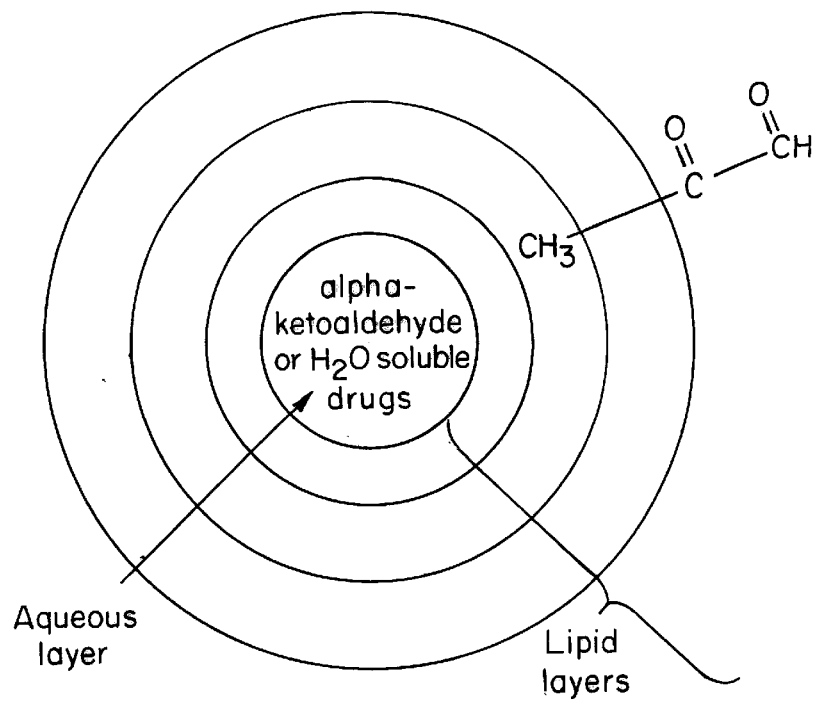
FIG. 1A is a schematic representation of a multilamellar physically latentiated alpha-ketoaldehyde.

The present invention is based on the findings that latentiated alpha-ketoaldehydes administered in vivo undergo specific reactions with camouflaged "nonself" cells. For the purpose of the subject application, a nonself cell is defined as a cell present within a vertebrate host, which is different from the host ("self") cell. This difference is expressed on the exterior of the cell via surface antigens. Thus, the surface antigens of nonself cells differ from the surface antigens of host, self cells. Examples of nonself cells include cancer cells, bacteria- or virus-infected cells, fertilized eggs and cells of lower organisms such as fungi, protists, parasites and bacteria.

In one reaction, latentiated alpha-ketoaldehydes remove and prevent the reformation of the host protein coating that camouflages many types of nonself cells. Once this coating is removed, the natural killer cells of the host's immune system are able to recognize and kill the nonself cells.

In another reaction, latentiated alpha-ketoaldehydes block protein synthesis, thereby inhibiting cell division. The lower homologues of alpha-ketoaldehyde (i.e., the aliphatic C-3 and C-4 homologues) may penetrate the cell wall and inhibit protein synthesis from within. The higher homologues (i.e., above C-5 of the aliphatic series) which do not penetrate the cell surface, together with the lower homologues, can block protein synthesis of a dividing cell by reacting with an arginine-rich protein. This protein appears on the cell surface at the initiation of cell division and is essential for cell division. (Stein, S. M. and Berestecky J. M., *Cancer Res.*:34: 3112 (1974); Stein S. M. and Berestecky J. M., *Cell Physiol*:85: 242 (1975)).

In a third reaction, the alpha-ketoaldehyde, methylglyoxal (MG) has been shown to inhibit tumor cell respiration in a selective manner. (Ray, M., et al.,*Int. J. Cancer,* 47:603–609 (1991); Kisch, B., *Biochem. Z,* 253:373 (1932)). It is reasonable to expect that latentiated alpha-ketoaldehydes would also be effective inhibitors of tumor cell respiration, resulting in destruction of nonself cells. Thus, alpha-ketoaldehydes, and particularly latentiated alpha-ketoaldehydes, present a triple threat to nonself cells. Furthermore, by providing three possible modes of interaction with nonself cells, resulting in destruction of nonself cells, latentiated alpha-ketoaldehydes afford increased potential to affect nonself cells exhibiting weak, or minimal, antigenicity.

As a result of these findings, it is now possible to use latentiated alpha-ketoaldehydes in therapies for treating diseases and conditions resulting from the presence of nonself cells in a vertebrate host. The following is a description of alpha-ketoaldehydes, methods of latentiating alpha-ketoaldehydes, and the mechanisms by which alpha-ketoaldehydes act in inhibiting the proliferation of nonself cells in a vertebrate host.

Alpha-ketoaldehydes

Alpha-ketoaldehydes are a series of chemicals derived from glyoxal (CHO—CHO), a dialdehyde with two carbon atoms. The simplest alpha-ketoaldehyde, methylglyoxal (2-oxopropanal), occurs naturally in small quantities inside normal cells. It is continually formed from several metabolic sources (Ohmori S, et al. "Biosynthesis and Degradation of Methylglyoxal in Animals" in Enzymology and Molecular Biology of Carbonyl Metabolism 2, (Ed: Flynn T. J.) Allan R. Liss Inc. Publisher, pp. 397–412 (1989)). Within a cell, alpha-ketoaldehydes function in regulating cell division. Based on this involvement in the internal self regulatory process of cell division, alpha-ketoaldehydes have been termed "autobiotics." (Egyud, L. G., *J. Biochem.*, 96:19c (1965); Egyud, L. G., *Proc. Natl. Acad. Sci. USA*, 54:200 (1965)).

Methylglyoxal ($CH_3COCHO$), with three carbon atoms (C-3), is the first member of an aliphatic series where each consecutive member is extended by a $CH_2$ unit (i.e., C-4, ethylglyoxal $CH_3$—$CH_2$—CO—CHO; C-5, propylglyoxal $CH_3$—$CH_2$—$CH_2$—CO—CHO; etc.). Members of the aliphatic series up to C-5 are soluble in water or lipid solvents. The higher members of the series (C-6 to C-12) are solids and soluble only in organic solvents. The reset of the synthetic compounds are reasonably soluble in water or a mixture of water/organic solvent.

Alpha-ketoaldehydes can be synthesized from the corresponding aldehydes or 2-ketones by known chemical methods (e.g., the selenious acid oxidation of N. Rabjohn (*Org. Reactions*, 5:331 (1949)) and H. L. Riley, et al. (*J. Chem. Soc.*, (1932)) by hydrolysis of alphaoximino ketones (Cox, *J. Chem. Soc.*, Vol. 129 (1936); Taylor, *J. Chem. Soc.*, (1926) or by cupric acid oxidation of 2-keto alcohols (Christaensen, et al., *Chem. Ind.* 1259, (1958) or US patents in *Chem. Abst.*, 51: 2072b (1957); Florkin, *Stotz Comphenz. Biochem.* 10: 85 (1963)). The alpha-ketoaldehydes can then be isolated by fractional distillation. The pure product, in cis and trans form, can be obtained by preparation gas chromatography. A number of alpha-ketoaldehydes (e.g., methylglyoxal, phenylglyoxal and hydroxymethylglyoxal) are also commercially available. Beta-substituted alpha-ketobutyraldehydes are available under the trade names "Kethoxal" and "Methoxal" (Upjohn Chemical, Inc., Kalamazoo, Mich.).

For the purposes of the subject invention, "alpha-ketoaldehyde" refers to a series of chemicals containing a ketone-aldehyde radical sequence attached to a greatly variable structure. Over 30 alpha-ketoaldehyde containing aliphatic, aromatic, heterocyclic, polycyclic moieties were synthesized and are described in U.S. Pat. No. 4,066,650, entitled "Keto-Aldehyde-Amine Addition Products and Method of Making Same", by Egyud, L. G. The teachings of the Egyud patent are incorporated by reference herein.

The preferred alpha-ketoaldehydes include, but are not limited to, methylglyoxal, phenylglyoxal and chlorinated derivatives, such as, chloromethylglyoxal, dichloromethylglyoxal, chlorophenylglyoxal and dichlorophenylglyoxal.

Latentiation

Alpha-ketoaldehydes are readily metabolized intracellularly to the corresponding β-hydroxy acids by glyoxalase enzymes in the presence of glutathione, which are present in all living cells (e.g., animal, plant and bacterial cells). Glyoxalase enzymes are especially active in red blood cells. However, alpha-ketoaldehydes can be modified so that they are protected against the action of glyoxalases while at the same time their in vivo toxicity is decreased and their specificity toward non-self cells (e.g., cells with increased surface —SH groups) is enhanced.

"Latentiation" refers to chemical or physical means of protecting the ketoaldehydic function of alpha-ketoaldehydes against significant modification or destruction by the in vivo environment. Latentiated alpha-ketoaldehydes, therefore, remain in a patient's blood stream longer than free alpha-ketoaldehydes.

Applicant has determined the half life of free and latentiated alpha-ketoaldehydes by injecting methylglyoxal radiolabelled with $^{14}C$ into mice. The in vivo decomposition of both free and latentiated methylglyoxal was followed by the appearance of radiolabelled $^{14}C$, which can be detected in the respiratory air or in the urine of the mice. With free alpha-ketoaldehydes, the half life was measured to be about 30 minutes. However, the half life of latentiated alpha-ketoaldehydes was measured to be at least 12 hours. Latentiation also protects host cells from the toxic effects of alpha-ketoaldehydes.

Latentiation can be accomplished chemically, physically, or by a combination of both chemical and physical means. For example, U.S. Pat. No. 4,066,650, the teaching of which are incorporated herein, describes chemically latentiated alpha-ketoaldehydes comprising addition products of monosubstituted ketoaldehydes with a secondary amine. Preferred chemically latentiated alpha-ketoaldehydes are methylglyoxal-glutaconic imide, and methylglyoxal-maleimide (also referred to as CaRest-M3™).

Alpha-ketoaldehydes can be chemically latentiated on reaction with primary amines. In these monosubstituted derivatives, only the aldehydic function is involved in an addition-type reaction. The formed aldimine proceeds further in anhydrous conditions to a labile Schiff's-base containing an azomethine linkage. The aldimine which formed rapidly under acid catalysis in water can liberate the ketoaldehyde in vivo upon the action of nonspecific amidases. However, the aldimine molecules are also subject to a slow uncontrollable polymerization forming a cyclic triazine derivative in water, even at neutral pH and low temperature. The cyclic derivative is stable, and there is no enzyme known to exist which has the ability to decompose the cyclic structure.

A surprising property of chemically latentiated alpha-ketoaldehydes is their ability to target nonself cells for elimination. Malignant tumor cells, and certain other nonself cells, are rich in surface sulfhydryl or thiol, groups (—SH) are compared with normal, or self, cells. (The presence of these —SH groups is associated with rapid cell division). The latentiated alpha-ketoaldehyde acts as a —SH scavenger which preferentially reacts with these highly reactive thiol groups on malignant and other nonself cells. For example, with methylglyoxal-maleimide, called the CaRest-M3™ agent by Applicant, the maleimide portion of the compound is the —SH reactive portion of the compound. Maleimide possesses two highly reactive pi-orbitals that enable maleimide to target —SH groups on cancer cells. The α-β carbonyl-activated pi-orbital over the C=C bond is the acceptor of the —SH group. When the latentiated methylglyoxal reacts with the —SH (thiol) group on the surface of a cancer cell (or other nonself cell), the highly interactive pi-orbital of the maleimide portion of the molecule binds strongly to the thiol, the pi-orbital collapses (i.e., the C=C bond changes to —C—C—), and the maleimide changes to a succinimide. This reaction eliminates the highly reactive pi-orbital system mentioned above.

The chemical structure and purity of these chemically latentiated alpha-ketoaldehydes can be verified by physical methods such as, but not limited to, CHN analysis, melting point, visible spectroscopy, uv-spectroscopy, liquid chromatography, IR-spectroscopy, nuclear magnetic resonance, mass spectroscopy, thin layer chromatography, and high pressure liquid chromatography.

The ketoaldehyde can also be modified to provide a potentially more potent latentiated alpha-ketoaldehyde. Modifications can include but are not limited to acetylation of methylglyoxal at the first carbon. For example, N-(1-hydroxyacetonyl) maleimide (the CaRest-M3™ agent, Compound A) and its acetylated derivative (Compound B) are shown below. This modification potentially allows the latentiated compound to pass more easily into the lymphatic system.

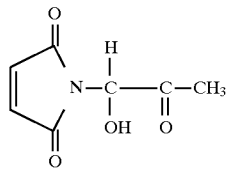
COMPOUND A

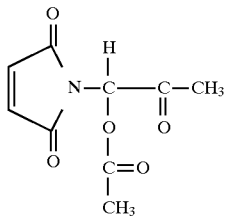
COMPOUND B

Both CaRest-M3™ and the acetylated derivatives can be further modified. The CaRest-M3™ agent may be modified at X as indicated below, by any of the following where X is —H; OH; CO—CH₃; —CH=CH₂; Cl; Cl₂; I; Br; NH₂; NH—R; N=R₂; or R (where R=(CH₂)₀₋₁₁—CH₃ or an aromatic or cyclic compound.

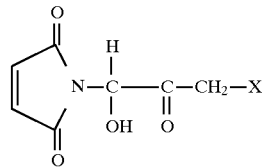

The acetylated derivative of CaRest-M3™ can be modified at position X as indicated below, where X is any one of the following: H; OH; OH; CO—CH₃; CH=CH₂; Cl; Cl₂; I; Br; NH₂; NH—R; N=R₂; or R (where R=(CH₂)₀₋₁₁—CH₃ or an aromatic or cyclic compound.

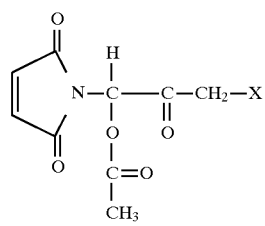

The use of halogens may increase potency by irreversibly reacting with a histidine residue near the active center of cysteine proteases. The modifications described herein can be made using standard art-recognized laboratory techniques.

Alpha-ketoaldehydes can also be physically latentiated. For example, an alpha-ketoaldehyde can be entrapped in an encapsulant, such as liposomes, starches and tissue-compatible synthetic chemicals (e.g., polymers). Encapsulants provide a controlled release of alpha-ketoaldehyde over an extended period of time. For example, the release of methylglyoxal from a polymethylmethacrylate encapsulant is complete only after about 175 hr. (Nozawa, Y. and Fox, S. W., *J. Pr. Sci.*, 70:385–386 (1981)). This controlled release to specific sites (i.e., targeted sites) limits the concentration of free alpha-ketoaldehyde in the blood stream at any point in time and therefore reduces toxic side effects and metabolization.

In a preferred embodiment, the alpha-ketoaldehydes are encapsulated and/or incapsulated in liposomes. Liposomes are formed from water insoluble polar lipids (e.g., phospholipids) in the presence of excess water. The highly ordered assemblages are arranged in a system of concentric closed membranes of an unbroken bimolecular sheet of lipid molecules separated from each other by water molecules. Liposomes may be prepared by a variety of techniques (Szoka, F., Jr., et al., *Ann. Rev. Biophys. Bioeng.*, 9:467 (1980); Willschut, J. in LIPOSOME METHODOLOGY, eds. Laserman, L. E. and J. Barbet, *INSERM*, Paris, p. 11 (1982)).

Figure 1B:
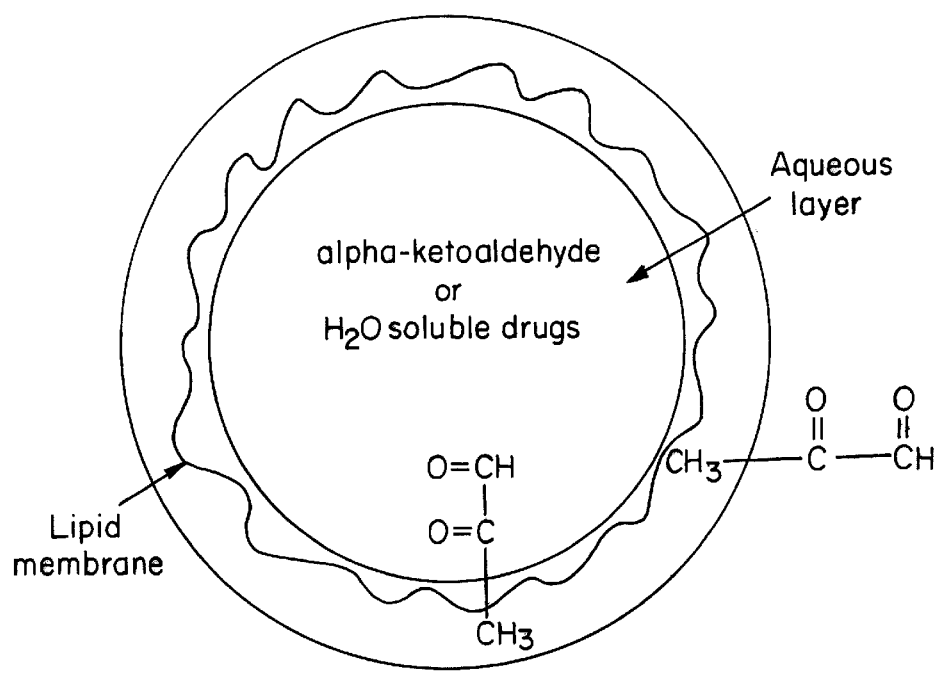
FIG. 1B is a schematic representation of a unilamellar physically latentiated alpha-ketoaldehyde.

Depending on the procedure used for preparation, liposomes consist of one or more lamellae (FIGS. 1A and 1B). All liposomes, whether multilamellar (FIG. 1A) or unilamellar (FIG. 1B), enclose an aqueous phase in which water-soluble substances can be encapsulated and released at variable rates. Alternatively, lipid soluble substances or water soluble molecules with hydrophobic moieties (e.g., drugs, chemotherapeutic agents or other alpha-ketoaldehydes) can be incorporated in the lipid phase of the liposome.

Liposomes can be prepared from a variety of amphophilic lipids. The most commonly used are the phospholipids, which are major components of biological membranes. The amphophilic nature of phospholipids, (i.e., the combination of a polar head and a hydrophobic tail within one molecule), is responsible for the bilayer arrangement upon hydration, where the hydrophilic heads are localized in both the outer part of the bilayer and the hydrophobic fatty acid chains are aligned directly opposite to each other in the inner part of the bilayer. Although any amphophilic lipid alone is sufficient for the formation of liposomes, the properties of the liposome can be improved by incorporating other water insoluble compounds into the structure. Therefore, liposomes can differ in dimensions, composition, charge (e.g., neutral, positive or negative) and structure (e.g., multilamellar, unilamellar).

Examples 1 and 2 of the subject invention describe in detail, methods of making liposomal alpha-ketoaldehydes. For the purposes of the subject invention, optimal liposomes should have a selected size between about 0.02–25 microns. Other standard, art-recognized methods of producing liposomes can also be used to make liposomal alpha-ketoaldehydes. Liposomal alpha-ketoaldehydes produced by the methods described herein, as well as other known methods can vary in composition and structure.

Liposomes injected into the body normally accumulate in the liver and spleen. Researchers have found that liposomes also congregate at sites of inflammation (Ostro, M. J. and P. R. Cullis, J. Hosp. Pharm. 46:1576–1587 (1989)). At sites of infection, inflammation and tumors, the body's vasculature is structurally compromised. It is reasonable to predict that liposome particles leak out of the vessels and become trapped in the surrounding tissue. It is thought that at this location, cells (e.g., macrophages) dispose of the liposome particles (Mertz, E. T., Biotechnology, Vol. 5, Page 6 (1987)).

Although sites in the body where nonself cells occur may also be sites of inflammation, when liposomal alpha-ketoaldehydes are injected in vivo, they have been found to specifically accumulate near nonself cells, in a degree greater than the degree to which liposomes not containing alpha-ketoaldehydes accumulate. That is, liposomal alpha-ketoaldehydes are also targeted to localize at nonself cells as do the chemically latentiated alpha-ketoaldehydes.

Preparation of liposomes in the presence of alpha-ketoaldehydes results in alpha-ketoaldehydes being "encapsulated" in the interior aqueous phase and also "incapsulated" in the lipid phase. Incapsulation produces CO—CHO groups, projecting out from the lipid surface (FIGS. 1A and 1B). The CO—CHO groups are highly reactive pi-orbitals. Therefore, these groups may act as a "homing" device, directing the alpha-ketoaldehyde laden liposome to the surface of the nonself cell surface attracted by the highly reactive —SH groups (Mehrishi J. N. and Grassetti, D. R., Nature, 224:563–564 (1969); Mehrishi J. N. Progress in Biophys. and Mol. Biol. 125:3 (1972)). The attached liposome can then enter or incorporate with the nonself cell by pinocytosis or fusion, whereupon the alpha-ketoaldehyde or other drug or chemical agent is liberated.

Enhanced delivery of other biologically active, water soluble molecules to nonself cells can be accomplished by incorporating the biomolecules into the aqueous phase, or lipid phase, of a liposomal alpha-ketoaldehyde.

Mechanism of Action of Latentiated Alpha-ketoaldehydes

The aldehydic function of an alpha-ketoaldehyde can react with thiol or amino groups. The ketonic function of an alpha-ketoaldehyde reacts with these same groups but to a lesser degree. The reaction of alpha-ketoaldehydes with thiols results in hemimercaptals, while reaction with primary amines results in very unstable aldimines or Schiff's bases. In proteins, alpha-ketoaldehydes react with arginine and/or the 5-amino group of lysine and the sulphydryl group of cysteine. In nucleic acids it reacts with guanine and its ribonucleic derivative. (Shauenstein, E. et al., ALDEHYDES IN BIOLOGICAL SYSTEMS, Pion Ltd., London, p. 115 (1977)). The reactions that occur between alpha-ketoaldehydes and protein thiols can lead to the deactivation of certain enzymes, in particular, sulphydryl enzymes such as tissue transglutaminase, cancer procoagulant and plasma transglutaminase (Factor XIIIa). (Shauenstein, E., et al., id; p.5).

Reactions between alpha-ketoaldehydes and cellular proteins result in a variety of important cellular changes. For example, alpha-ketoaldehydes inhibit cell proliferation primarily by reacting with the functional sulphydryl groups involved in protein biosynthesis (Shauenstein, E., et al., ALDEHYDES IN BIOLOGICAL SYSTEMS, Pion Ltd., London, p. 122 (1977)). Strong inhibition of protein synthesis by alpha-ketoaldehydes occurs in vitro at concentrations which do not influence cell respiration or intermediary metabolism. The length of inhibition is dependent on the cell number relative to the amount of alpha-ketoaldehyde present in the medium (Otsuka, H. and Egyud, L. G., Cancer Res., 27:1498 (1967); Otsuka, H. and Egyud, L. G., Curr. Mod. Biol., 2:106 (1968)). Inhibited cells resume division upon addition of thiol containing compounds (e.g., 1, 2-dithioethane, cysteamine, British antileusite (BAL), cysteine) but not with glutathione, suggesting the involvement of cellular —SH radicals in the inhibitory process.

Alpha-ketoaldehydes have also been shown to inhibit tumor cell respiration. Tumor cells are known to exhibit an unusually high rate of aerobic glycolysis in comparison with normal cells. (Ray, M., et al., Int. J. Cancer, 47:603–609 (1991)). It appears that the alpha-ketoaldehyde interferes with tumor cell glycolysis. As a consequence, the respiration of malignant cells is inhibited, thereby inducing cell death. Alternatively, the alpha-ketoaldehyde may directly inhibit the mitochondrial respiration of tumor cells. (Ray, M., et al., Int. J. Cancer, 47:603–609 (1991)). It is reasonable to expect that latentiated alpha-ketoaldehydes would also be effective inhibitors of tumor cell respiration.

Inhibition of cell division is probably also due to reactions between alpha-ketoaldehydes and arginine rich proteins that appear on the surface of cells during the S and G-2 phases of mitosis (Stein, S. M. and Berestecky, J. M., Cancer Res., 34:3112 (1974); Stein, S. M. and J. M. Berestecky, J. M., J.Cell Physiol., 85:243 (1975)). Stein and co-workers found that reacting phenylglyoxal, an alpha-ketoaldehyde that cannot enter cells with the arginine rich proteins, results in cells that can not divide, and which become "leaky" and die.

All of the alpha-ketoaldehydes tested thus far have been found to inhibit cell division in varying degrees, indicating that the biological activity rests with the CO—CHO function. The cell surface is the primary site for inhibition of cell division by alpha-ketoaldehydes which cannot penetrate the cell membrane (i.e., homologues above C-5 of the aliphatic series). Their inhibitory effect on cell division is entirely dependent on reactions with cysteine, arginine, lysine and histidine residues on the cell surface. The lower homologues of the aliphatic series (e.g., C-3 and C-4) penetrate the cell wall. Their inhibitory effect may depend both on the exterior and the interior receptors of the cell. Inhibition of cell proliferation by alpha-ketoaldehydes has been shown for a number of bacteria, molds, yeast, plants and animal cells in tissue culture.

Tumor, or malignant, cells have been found to be 10–12 times more sensitive to inhibition by alpha-ketoaldehydes than normal cells (Shapiro, R., Ann. N.Y. Acad. Sci., art. 2, p. 624 (1969)). This may be due to the fact that cancer cells have excess amino and thiol groups on their surface (i.e., more than normal dividing cells). This may also be due to the lower than normal glutathione content of tumor cells. Glutathione gives a protective effect to cells from —SH scavengers.

For cell division, the physical status of the cell changes involve both the interior and the membrane of the cell. Because of decreased cohesion, due to liberation of —SH radicals from —S—S— linkages, the interior of a cell becomes semi-liquid so that the inner components can move and rearrange themselves. At the same time, the cell membrane also changes. The cell surface becomes repulsive in order to be able to move independently of the surrounding cells. The dividing cell surface changes so as to break the intercellular disulfide bonds to —SH which detach the dividing cell from the adjoining cells. For normal cells, after cell division is completed, the interior and cell surface revert to the activity level and structure that existed before cell division. As a result, cells formed from the division reattach with the adjacent cells and the surface bonds return to the normal values. However, if a cell becomes malignant for any reason, the cell does not revert to the normal state after division. This means that the surface of malignant cells do not have the normal attachment properties (i.e. contact inhibition). As a result, the malignant cell is free to metastasize and move around to other locations or organs in the body. In addition, because nonself cells are unattached, they also have more free —SH groups on their surface (Mehrishi, J. N. and Grassetti, D. R., *Nature*, 224:563–564 (1969); Mehrishi, J. N., *Progress in Biophys. Mol. Biol.*, 25:3 (1972)).

The presence of viruses or bacteria in cells results in an altered MHC Class-I on the surface of the cell (Townsend, A., IMMUNE RECOGNITION AND EVASION: MOLECULAR ASPECTS OF HOST-PARASITE INTERACTIONS (1990) eds: Lex et al. p. 87, Academic Press). It is also reasonably possible that the presence of viruses or bacteria in cells is similarly correlated with an increased number of —SH groups on the surface of an infected cell. Nonself cells may often have excess amino and thiol groups on their cell surface. Therefore, nonself cells would be much more sensitive to inhibition by alpha-ketoaldehydes than self cells. This is a reasonable explanation for the selective non-toxicity of latentiated alpha-ketoaldehydes at therapeutic levels.

Cells which are either invaded by microorganisms (i.e., bacteria, viruses, etc.) or cells which for various reasons have altered cell surfaces (e.g., malignant cells, fertilized eggs) are "foreign" or "nonself" to the host. Altered, or nonself cells, are routinely recognized as foreign in vivo, and are normally marked, destroyed and eliminated by cells of the Immune Surveillance System. However, some nonself cells resist the immune system of a host by attaching host protein to their "foreign", transplantation antigenic site.

Figure 2:
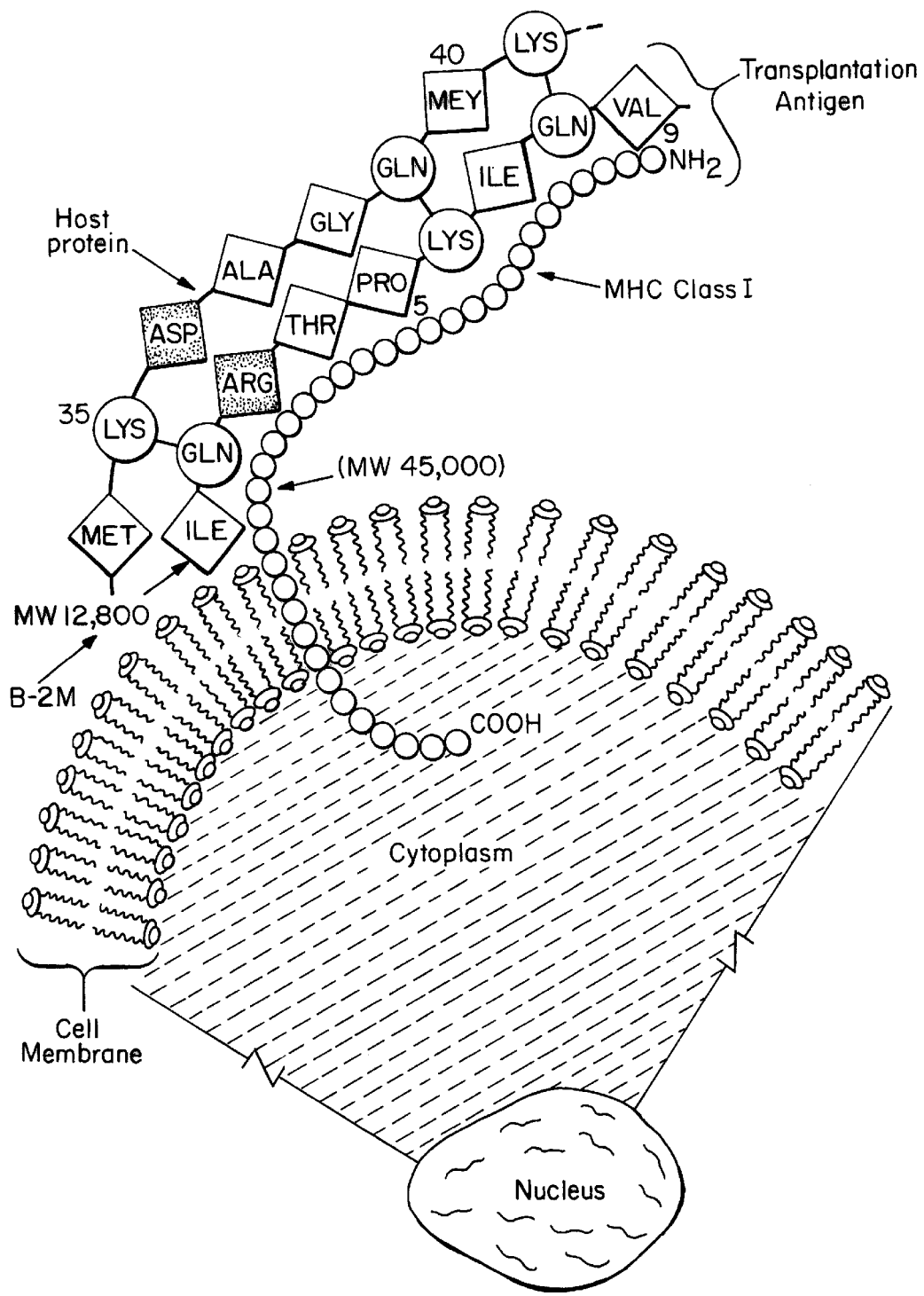
FIG. 2 is a diagram representing the attachment of host protein to the transplantation antigen of a nonself cell.

FIG. 2 is a diagram representing the attachment of host protein to a nonself cell's transplantation antigen. Although the figure only depicts one transplantation antigen, a cell usually contains many such sites. The transplantation antigen is made up of two proteins: Beta-2-microglobulin (B-2-M); and the major histocompatibility complex I (MHC-Class I). The B-2-M is electronically (i.e., via Van der Waal's forces) associated with the MHC-Class-I of the host cell. The host protein is attached to the B-2-M by covalent isopeptide linkages between the gamma carboxylic group of glutamic acid and the epsilon amino group of lysine. The isopeptide linkages between the adjacent protein chains are formed by the action of a sulfhydryl enzyme, tissue transglutaminase, present in the cell membrane. The attachment of host protein to the transplantation antigen "camouflages" the nonself cell so that it is not recognized by the cells of the host's immune system (e.g., natural killer cells, activated T4 and T6 cells).

Figure 3:
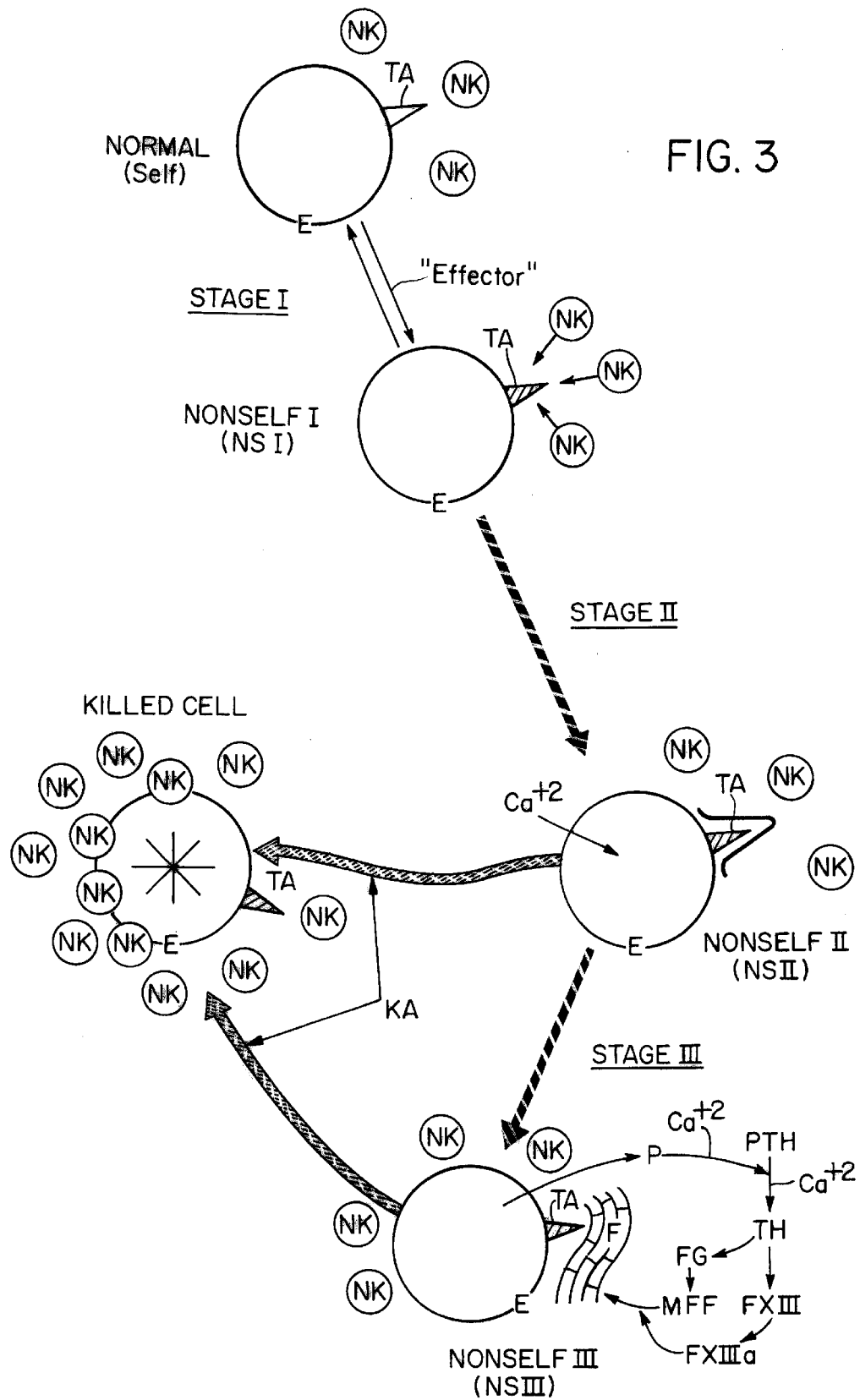
FIG. 3 is a diagram representing the camouflaging of a nonself cell with host protein and the removal of the camouflage upon reaction with an alpha-ketoaldehyde (KA).

FIG. 3 is a diagram representing the camouflaging of a nonself cell and the removal of the camouflage upon reaction with an alpha ketoaldehyde. Stage 1 of FIG. 3 shows a self cell that is made Nonself I (NS-I) by interaction with an "effector". Effectors include, for example, viral, bacterial, parasitic or fungal pathogens, tumor causing agents, or sperm. Other nonself cells include fertilized eggs.

The difference between a nonself cell and a self cell is expressed in the transplantation antigens (TA). Host natural killer (NK) cells generally recognize the different transplantation antigens of nonself cells. Thus, the NK cells specifically kill nonself cells.

However, the Nonself I (NS-I) cell may escape recognition by becoming camouflaged. The cell camouflage is accomplished in two distinct steps. In the first irreversible step (stage 2 of FIG. 3), tissue transglutaminase (E), an enzyme present in the cell membrane activated by calcium ion influx, attaches any available host protein to the B-2-M (depicted in FIG. 2), transforming the cell to Nonself II (NS-II). The attached host protein hides the recognition sites from the NK cells, so the cell is not recognized as "foreign".

However, a single protein coat, as occurs in NS-II cells, may not protect cells well enough against highly active NK cells. Therefore, a fortified cell coat is made of multilayered protein. In the second step, NS-II cells are transformed to Nonself III (NS-III). In stage III, the NS-II cell excretes a protein, procoagulant (P), which, in the presence of calcium ions, is able to shortcut hemostasis on the cell surface by directly activating Factor X. Activated Factor X (FXa), catalyzes the conversion of prothrombin (PTH) to thrombin (TH). Thrombin catalyzes two reactions: the conversion of proenzyme Factor XIII (F-XIII) to plasma transglutaminase Factor XIIIa (F-XIIIa); and the conversion of fibrinogen (FG) to monofilamentous fibrin (MFF) over the NS-III site. Monofilamentous fibrin (MFF) has no three dimensional tensile strength. Therefore monofilamentous fibrin (MFF) is cross-polymerized by Factor XIIIa (FXIIIa) to a three dimensional, multilayered fibrin clot in situ. The stable fibrin clots surround and provide additional camouflage to the Nonself III (NS-III) transplantation antigen.

However, by reacting with the sulphydryl groups at the active site of cysteine proteases, (i.e. transglutaminase enzymes and procoagulant), alpha-ketoaldehydes deactivate the enzymes. Latentiated alpha-ketoaldehydes and their derivatives can cause the removal and prevent the reformation of the fibrin "cover" over the transplantation antigenic sites. Without the protective coat, the "nonself" sites are exposed to foreign cell recognition and destruction by NK cells of the host's immune system (represented in FIG. 2 as the "killed cell").

The role of transglutaminase in masking the nonself antigenicity of a mammalian fertilized egg so that it may successfully complete implantation, angiogenesis and placenta formation, has been well documented (Lampe, L., *Szuleszet es nogyogyaszat*, (Obstetrics and Gynecology) Vol. I, p.6, Medicina Publisher, Hungary (1981)). The egg becomes nonself upon cell fusion with the "effector" sperm (stage 1 of FIG. 2). The nonself conceptus is originally coated with uteroglobulin, a protein found in abundance between the 12th–18th days of menses in the uterus (stage 2). This covering then changes over to fibrin-like material (stage 3) after the fertilized egg is implanted. Fibrin formation around the fertilized cell is the result of local activation of hemostasis by a fertilized egg produced procoagulant. A layer, called Nitabuch's fibrin layer is present in the decidua even at the 36th week of pregnancy separating the conceptus from the mother. (Lampe L. in *Szuleszet es nogyogyaszat* (Obstetrics and Gynecology) Vol. I, p.96, Medicina Publisher, Hungary, (1981)).

The "two-step" masking procedure is also well documented in cancer cells. Normal cells become cancerous by interacting with an effector (e.g., carcinogens, radiation such as X-ray, UV and $\alpha$ and $\beta$ radiation, etc). In the first step of the camouflage (stage 2), altered cells can pick up any protein available in the circulation and bind it to the newly developed antigenicity site by a reaction catalyzed by tissue transglutaminase. Once the altered cell becomes malignant, cancer procoagulant is produced. As depicted in stage 3 of FIG. 2, cancer procoagulant (P) activates hemostasis and fibrin is deposited around and in the vicinity of the tumor cell. This fibrin can serve as a physical barrier to cells of the immune system (Gordon, S. G., *Cancer Procoagulant*, in *HEMOSTASIS AND CANCER* (ed. L. Muszbek) CRC Press, p. 19 (1987)).

A similar protein deposition sequence by tissue transglutaminase and procoagulant can be induced in cells attacked by agents which penetrate, or attach to, host cell membranes (e.g., bacteria, viruses, parasites, fungi, etc.) or on the surface of free living, noncell-penetrating agents (e.g., parasites, fungi, bacteria, etc.) used for their own defense.

In sum, once targeted to localize at a nonself cell, there are three modes by which latentiated alpha-ketoaldehydes attack in vivo. In one mode, protein synthesis is inhibited, thereby preventing growth and proliferation of the nonself cell. In the second mode, latentiated alpha-ketoaldehydes remove and prevent the reformation of the protective coating camouflaging nonself cells. Once this coating is removed, the nonself cells are exposed to recognition, attack and destruction by the host's natural killer cells. In the third mode, nonself (e.g., tumor cells, bacteria- and virus-infected cells) cell respiration is inhibited.

Therefore, whereas with many conventional chemotherapies, the patient's normal immune response is eliminated or reduced, chemotherapies based on alpha-ketoaldehydes actually enable the patient's own immune response to recognize and destroy foreign malignant cells.

Utility

Latentiated alpha-ketoaldehydes, can be useful in controlling any disease or condition resulting from the presence of nonself cells in a host. The use of latentiated alpha-ketoaldehydes for treating diseases resulting from the presence of nonself cells is advantageous because alpha-ketoaldehydes are found naturally in host cells and, therefore, do not initiate a defense mechanism in nonself cells.

Administration of latentiated alpha-ketoaldehydes can be useful in treating any diseases such as but not limited to: cancer, viral diseases (e.g., AIDS, influenza, measles, herpes, mumps, chicken pox, shingles, hepatitis), bacterial diseases (e.g, pneumonia, bronchitis, meningitis, carditis, periodontitis, bovine mastitis), fungal diseases (e.g., histoplasmosis, blastomycosis, candidiasis), and parasitic diseases (e.g., malaria, filariasis, leishmaniasis, trypanosomiasis). These diseases all result from the infection of vertebrate cells with organisms that cause alterations in vertebrate cell surface features, and subsequent proliferation of those nonself cells in the vertebrate host.

An advantage of using latentiated alpha-ketoaldehydes in treating diseases caused by the presence of nonself cells in a host is that latentiated alpha-ketoaldehydes, both chemically latentiated and physically latentiated, have specific targeting properties. This targeting ability results in enhanced, localization of the alpha-ketoaldehyde at nonself cells.

Another potential advantage in using latentiated alpha-ketoaldehydes is that some latentiated alpha-ketoaldehydes (particularly small molecular forms) may pass the blood/brain barrier and may enter into the lymphatics localizing at non-self cells present in the brain or the lymphatics.

Malignancy results when a vertebrate's own cells become nonself. Therefore, latentiated alpha-ketoaldehydes could be used as an antineoplastic agent. Example 3 describes the effect that methylglyoxal (MG) and liposomal methylglyoxal (L-MG) have on tumor-bearing mice. Both MG and L-MG were found to be equally potent in topical treatment. However, L-MG was found to be far more effective in systemic treatment of tumors. Also, L-MG treated tumor-bearing mice were found to be resistant to reformation of tumors. Apparently an immunity is also produced when a malignancy is treated with latentiated alpha-ketoaldehydes. This immunity could prove important in preventing reoccurrence of malignancy.

In a preferred embodiment, the chemically latentiated alpha-ketoaldehyde (methylglyoxal-maleimide, or the CaRest-M3™ agent) can be used as an effective antineoplastic agent. CaRest-M3™ has been studied and its biological effects verified against a variety of human tumor cell lines in vitro.

As described in detail in Example 4, the CaRest-M3™ agent was treated by the National Cancer Institute (NCI) against human tumor cell lines, derived from eight cancer types (lung, colon, melanoma, renal, ovarian, brain, prostate and leukemia). CaRest-M3™ demonstrated both tumor growth inhibition and tumor cell killing against all eight cancer types tested. The initial screen results were verified at NCI by a subsequent screen under identical conditions.

The CaRest-M3™ agent has also been shown to inhibit the colonization of B16 melanoma and Lewis lung carcinoma cells in the lungs of mice, and to increase the survival time of mice injected intravenously with these tumor cells. As described in detail in Example 5, mice were inoculated with B16 melanoma or Lewis lung carcinoma cells. Twenty-four hours after tumor implantation, mice were divided into groups and treated with CaRest-M3™ or control solutions.

As shown in Example 5, Tables 2–6, mice treated with the CaRest-M3™ agent survived significantly longer, including a significant percentage of tumor-free survivors, and had significantly lower lung colony counts and lung tumor weights than the control mice.

Figure 4:
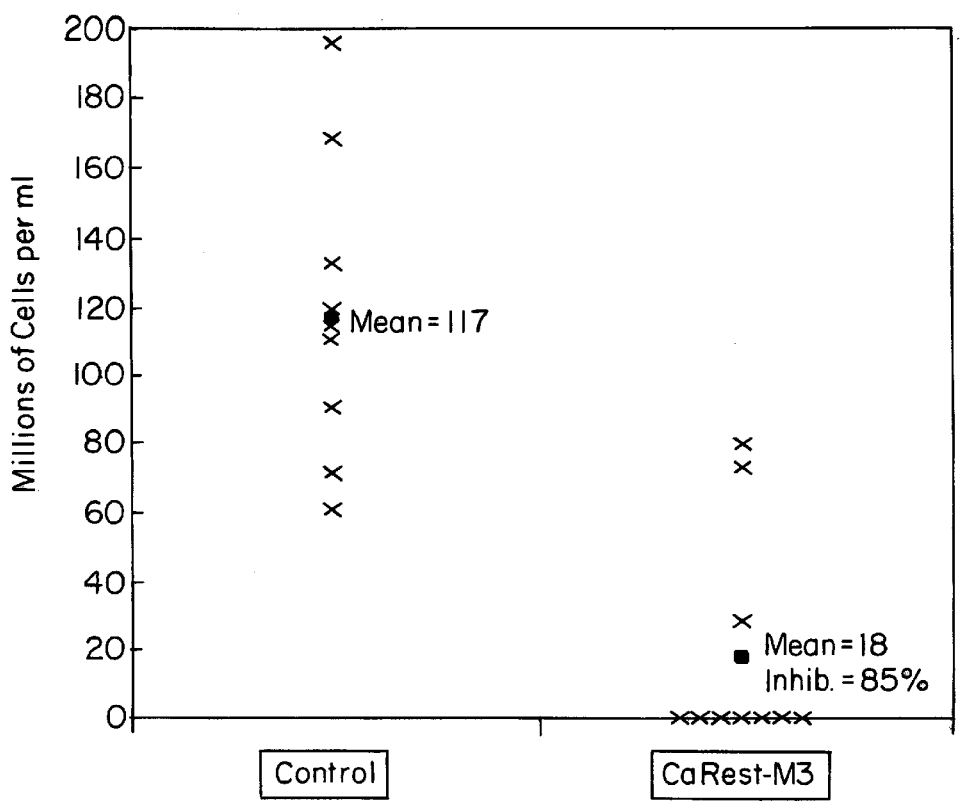
FIG. 4 is a graphic representation of the effect of chemically latentiated methylglyoxal on intraperitoneal Ehrlich ascites carcinoma in mice.

Latentiated alpha-ketoaldehydes were further tested for their ability to inhibit growth of Ehrlich ascites carcinoma cells in mice. As described in detail in Example 6, mice were inoculated with Ehrlich ascites tumor cells. Subsequent treatment of these mice with the CaRest-M3™ agent resulted in significant inhibition of tumor growth and tumor-free survivors as compared to control mice. (FIG. 4).

Latentiated alpha-ketoaldehydes have also been tested in pilot clinical trials, treating dogs with naturally-occurring spontaneous tumors. As described in detail in Example 7, five dogs, one with a metastatic squamous cell carcinoma and four with malignant melanomas, have been treated with the CaRest-M3™ agent. After two, ten-day courses of treatment with CaRest-M3™, the dog with the squamous cell carcinoma has been judged to be in complete remission ten months post-treatment. Of the four dogs with malignant melanoma, 3 have shown tumor regression, or stable disease 2–6 months post-treatment. (The fourth dog was euthanized by the owners one month after treatment).

Latentiated alpha-ketoaldehydes can be used as an antineoplastic agent in place of surgery, or after the surgical removal of a tumorous growth. Latentiated alpha-ketoaldehydes can also be effective in the control and prevention of new metastases which may arise as a consequence of "surgical spilling", or at metastatic sites already existing as non accessible tumors, or to prevent the metastasis of a tumor.

Figure 5:
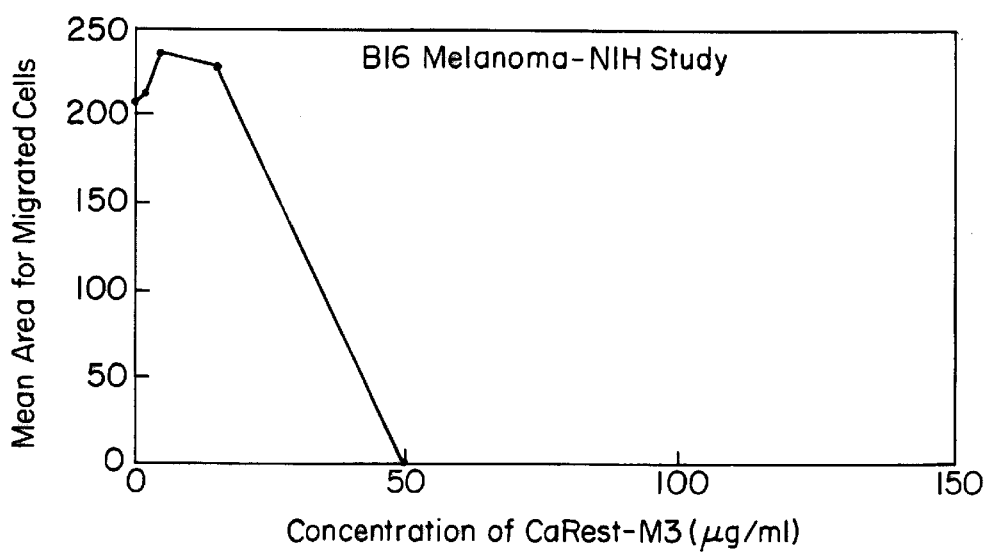
FIG. 5 is a graphic representation of the effect of methylglyoxal-maleimide on B16 melanoma tumor cell migration.

As described in detail in Example 8, and in FIG. 5, the latentiated alpha-ketoaldehyde CaRest-M3™ is effective in inhibiting B16F10 tumor cell migration and cell adhesion, which are two factors which play critical roles in tumor cell metastasis. Thus, it is reasonable to predict that if latentiated alpha-ketoaldehydes inhibit tumor cell migration and adhesion, they will be effective against tumor cell metastasis.

Alpha-ketoaldehydes can further be used as a non-steroidal birth control device. At an early phase of embryonic development, fertilized eggs develop into a "trophoblast." The outer layer of a trophoblast consists of a monolayer of specialized cells whose function is to implant the developing embryo into the uterine wall, provide arterial and venous blood connections and to initiate formation of the placenta. These aggressive, fermentative and invasive cells are comparable to tumor cells because they camouflage their outer surface with host protein. As described in Example 9, daily administrations of latentiated alpha-ketoaldehyde to pregnant female mice resulted in 83.3% of the pregnancies being inhibited.

Latentiated alpha-ketoaldehydes can also be effective in male contraception. The sperm head contains chromatin, which is normally in a condensed state. However, during fertilization, the chromatin must decondense or unravel, upon entering the egg. As shown in Example 10, the CaRest-M3™ agent causes a hyperstabilization of sperm chromatin which prevents the decondensation of the chromatin. These results indicate that latentiated alpha-ketoaldehydes may decrease male fertility by inhibiting the necessary decondensation of the sperm head after it has entered the egg.

Alpha-ketoaldehydes are also useful as radiosensitizers. Experiments described in Example 11 show that administration of alpha-ketoaldehydes to a vertebrate host results in an increased effectiveness of radiation treatment by a factor of about 5 to 10. Therefore, administration of alpha-ketoaldehydes in conjunction with radiation treatment will permit lower radiation dosages resulting in reduced side effects such as nausea, hair loss and healthy tissue damage due to radiation treatment. It is reasonable to expect that administration of latentiated alpha-ketoaldehyde will give similar results.

Latentiated alpha-ketoaldehydes can also be effective in minimizing the rejection of transplanted tissues (e.g., skin, pancreas, liver, kidneys, heart, lung and bone marrow). The presence of alpha-ketoaldehydes in vivo inhibits protein synthesis and thus antigen formation, which is responsible for the initiation of the rejection mechanisms. Administration of latentiated alpha-ketoaldehydes before, during, and for, a short period of time after transplantation (e.g., 60 days) would obviate the need for rejection fighting drugs. Latentiated alpha-ketoaldehydes can be administered as needed until the transplant or graft over time becomes "self". Thus, administration of latentiated alpha-ketoaldehydes may reasonably facilitate intra- and inter-species tissue transplants without depression of the immune system.

Example 12 describes an experiment in which a chemically latentiated alpha-ketoaldehyde, CaRest-M3™, was administered intraperitoneally to mice undergoing skin transplants. Mice were pretreated for 10 days prior to transplantation, followed by 25 days post-transplant treatment. As shown in Table 12, no rejection of the graft was observed on days 26–30 and 10% rejection was observed on days 31–40. Importantly, the tissue acceptance continued even after the latentiated alpha-ketoaldehyde was no longer administered. Apparently the use of the latentiated alpha-ketoaldehyde also permitted the foreign tissue to be adopted.

Latentiated alpha-ketoaldehydes can also be used to inhibit the growth of molds. Many *L. penicillium,* a genus of molds, are sometimes found as parasites on man (i.e., *Penicillium montoyai, P. buffardi, P. minimum,* etc), others like *P. notatum,* are used in the cheese industry. *L. aspergillus,* a genus of ascomycetous fungi, includes several of the common molds. Some of them are similar to *Aspergillus auricularis, A. barbae, A. mucoroides,* etc.). *A. niger* found in the external ear causing otomycosis. It also causes diseases in animals that consume grain infected with it.

As described in Example 13, latentiated alpha-ketoaldehydes effectively inhibited the growth of *Penicillium notatum* and *Aspergillus niger.*

Latentiated alpha-ketoaldehydes can also be used to inhibit growth of yeast. *Candida albicans* (e.g., *C. cerviceae*) is a yeast present in over 90% of normal human GI tracts. The number is kept relatively constant by the immune surveillance system. Moreover, immune suppressors, like anti-neoplastic drugs, often cause generalized candidiasis of immune compromised patients (15–35% of leukemic patients die of candidiasis). Other cancers also have high *C. albicans* infection as a cause of death.

Candidas are very potent yeasts that will adapt to most conditions readily, and are quite refractory to antibiotics. 5-fluorocytosine (5FC), is a potent agent, but has a short-lived action. It penetrates the cell wall of *C. albicans,* but not human cells. Thus, although it exhibits low toxicity to the host, after its short-lived action, *C. albicans* adapts. As described in detail in Example 14, latentiated alpha-ketoaldehydes are effective inhibitors of *C. albicans* growth.

Latentiated alpha-ketoaldehydes are further useful as anticoagulants. As explained in conjunction with FIG. 2, alpha-ketoaldehydes react with the sulphydryl groups of transglutaminase enzymes. In so doing, the alpha-ketoaldehydes modify the formation of fibrin. Thus, it is reasonable to predict that latentiated alpha-ketoaldehydes administered in vivo to a vertebrate can be used as a prophylactic against blood clot formation and may promote blood clot dissolution.

Example 15 describes an experiment showing the effect alpha-ketoaldehydes have on blood coagulation. Clotting times of alpha-ketoaldehyde treated plasma were compared to clotting times of control plasma. Chloromethylglyoxal and dichloromethylglyoxal were found to be the most effective anticoagulants. It is reasonable to predict that latentiated alpha-ketoaldehydes would also be effective anticoagulants.

Tissue transglutaminase has been implicated in the skin disease, psoriasis. As described in Example 16, alpha-ketoaldehyde significantly inhibits tissue transglutaminase activity in vitro. It is reasonable to predict that latentiated alpha-ketoaldehydes would inhibit tissue transglutaminase activity in vivo. For treatment of psoriasis, in a preferred embodiment, the alpha-ketoaldehyde is formulated for topical application to the affected area.

Latentiated alpha-ketoaldehydes can also be used in the treatment of parasitic diseases. As described in detail in Example 17, CaRest-M3™ agent inhibits the viability of the parasite, *Brugia Malayi* at concentration as low as 0.1 mM.

Furthermore, as described in detail in Examples 18–20, latentiated alpha-ketoaldehydes are not toxic to animals at the dosages used in the methods described herein. Toxicity studies were performed in rats (Example 18), mice and dogs (Example 19).

Alpha-ketoaldehydes are generally administered to vertebrate animals, including but not limited to fish, avians and mammals, including humans. The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, polyvinyl pyrrolidone and the like.

The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined with other active agents, such as, enzyme inhibitors, to further reduce metabolic degradation.

For parenteral administration, injectable sterile solutions, preferably oily or aqueous solutions, as well as suspensions, emulsions, or implants, including suppositories are particularly suitable. Storage in ampules can provide convenient unit dosages.

For enteral application (including application via oral and nasal mucosa), particularly suitable are tablets, liquids, drops, suppositories or capsules or tablet. A syrup, elixir or the like can be used with a sweetened vehicle. For oral administration, the latentiated alpha-ketoaldehyde can be formulated so that the latentiated alpha-ketoaldehyde is contained within an encapsulant and released in the intestine and/or the stomach, with controlled release localized at nonself cells, such as with time-release capsules. Latentiated alpha-ketoaldehydes may also be administered subcutaneously or transcutaneously.

For topical application, nonsprayable forms, viscous to semisolid or slid forms comprising a carrier compatible with topical application and having a dynamic viscosity preferably greater than water can be used. Suitable formulations include, but are not limited to, solutions, suspensions, emulsions, creams, ointments, powders, liniments, salves, aerosols, etc. These formulations can be sterilized, or mixed, with auxiliary agents, such as preservatives, stabilizers, wetting agents, buffers or salts for influencing osmotic pressure. For topical application, sprayable aerosol preparations wherein the active ingredient, preferably in combination with a solid or liquid inert carrier material, is packaged in a squeeze bottle or in admixture with a pressurized volatile, normally gaseous propellant. Topical applications may also include dermal patches or subcutaneous tissue implants.

The average daily dose of physically latentiated alpha-ketoaldehyde as determined with mice (26 g±2 g body weight) is 200–260 mg/kg i.v. or i.p. The average daily dose of chemically latentiated alpha-ketoaldehyde is 3–6 mg/kg i.v. or i.p. for mice and for dogs is 0.3–0.5 mg/kg i.v. These values can be converted for other species by using a conversion chart which is based on the equivalent body surface, establishing the "body surface area-dose" relation (Freireich, E. J. et al., *Can. Chem. Therap. Rep.,* 50:219 (1966)). The actual preferred amounts of active compound in a specific case will vary according to the specific compound being utilized, the particular compositions formulated, the mode of application, and the particular situs and organism being treated. Dosages for a given host can be determined using conventional considerations, e.g., by means of an appropriate, conventional pharmacological protocol.

The courses of treatment with latentiated alpha-ketoaldehyde can include a single course of treatment, with daily doses of latentiated alpha-ketoaldehyde over a period of time (e.g., 10–20 days) as well as multiple courses of treatment (e.g., a first course of treatment for 10–20 days, followed by a second course of treatment within one to two weeks of the end of the first course of treatment. The courses of treatment can comprise alpha-ketoaldehyde alone, or in conjunction with other chemotherapeutic or radioisotopic treatment.

The present invention will now be illustrated by the following examples, which are not intended to be limiting in any way.

EXAMPLE 1

Production of Liposomal Methylglyoxal (L-MG)

The lecithin-cholesterol-methylglyoxal ratio of the following liposomal methylglyoxal is 6:2:3 w/w/w (weight/weight/weight). The methylglyoxal and cholesterol contents are variable over a wide range. For example, the methylglyoxal content can vary from 0.5 to 4, while the cholesterol content may also vary from 0.5 to 3 weight ratios. The lecithin content, however, is not variable.

First, six grams of egg lecithin (Sigma) and 3 grams of cholesterol (Sigma) are dissolved in chloroform.

At this point either of the following two procedures can be used:

1. To the solution, 3 g of methylglyoxal in water (7.5 ml 40% aqueous solution, Aldrich) is added, the pH is adjusted to 6.5 with sodium bicarbonate and mixed. The water is removed from the mixture by repeated azotropic distillation in a vacuum at bath temperature (not exceeding 30° C.). The residue is taken up in chloroform and solvent evaporated as above. The steps are repeated 3–4 times so that all water is removed. To the resultant lipid film, containing the methylglyoxal, 0.9% saline is added, shaken by hand, and sonicated (on ice for 9 min., sonic power output 1500–2000 decibels) after the final volume is adjusted to 130 milliliters.

2. The chloroform is removed by vacuum distillation (bath temperature, 20° C.). To the resultant lipid film three grams of methylglyoxal (7.5 ml 40% aqueous solution, Aldrich) is added, the pH adjusted to 6.5 with sodium bicarbonate and then diluted to 100 ml with 0.9% saline. The lipid film in the round bottomed flask is suspended into the water by handshaking, followed by sonication (on ice for 9 min.; sonic power output 1500–2000 decibels) of the suspension. The final volume of the sonicate is adjusted to 130 ml with saline.

The sonicated liposome suspension is centrifuged at 10° C. for 2 hrs. (10,000 RPM). The supernate is collected and the amount of methylglyoxal present in the solution is estimated by Friedman's titration method (Friedman, T. F. J., *J. Biol. Chem.* 73:331 (1927)). The precipitate is resuspended into 100 ml saline and centrifuged (60 min. at 10° C., 10,000 RPM). The collected precipitate is resuspended into saline at a concentration required for in vivo treatment.

EXAMPLE 2

Production of Liposomal Phenylglyoxal

The lecithin-cholesterol-phenylglyoxal (PhG) ratio of the following liposomal phenylglyoxal is 6:2:2 w/w/w, (weight/weight/weight). Egg lecithin (360 mg), cholesterol (120 mg) and phenylglyoxal monohydrate (136 mg) are mixed and dissolved in chloroform. (Phenylglyoxal is soluble in chloroform methanol and ethanol and is sparingly soluble in water). The chloroform is removed by evaporation in a vacuum at room temperature, resulting in a thin film in the round bottomed flask.

The thin film containing the phenylglyoxal is mixed with 20 ml 0.9% saline, shaken by hand, and the resultant suspension is sonicated for 2 minutes on ice. The formed liposome suspension is centrifuged at 10° C. for 2 hours at 10,000 RPM. The supernate is collected and the phenylglyoxal present in the solution is estimated by Friedman's method. The amount of phenylglyoxal in the precipitate is calculated and it is resuspended in 0.9% saline at a required concentration and stored at room temperature. In a typical experiment, 4 mg/kg of latentiated phenylglyoxal is used for in vivo treatment.

The liposomes containing phenylglyoxal are stable for 56 days at room temperature. After longer storage, a precipitate is formed which can be resuspended on sonication.

EXAMPLE 3

In Vivo Treatment of Tumors with Physically latentiated Methylglyoxal

Methylglyoxal, which is equally soluble in both the aqueous and the lipid phase, was encapsulated into liposomes of 8–20 microns in diameter as explained in detail in Example 1. Groups of mice were inoculated with Sarcoma-180 cells either subcutaneously (sc) or intraperitoneally (ip) (3 million cells; 89% viability) followed by intravenous (iv) or intraperitoneal treatment with methylglyoxal (MG) of liposome encapsulated methylglyoxal (L-MG) (10 days, 250 mg/kg per mouse per day, Table 1).

TABLE 1

| S-180 cell inoculation | ip ip (topical) | | sc iv (Systemic) | |
| --- | --- | --- | --- | --- |
| treatment | T/C % | I % | T/C % | I % |
| control | 100 | 0 | 100 | 0 |
| MG | 0.0043 | 99.9 | 87.6 | 12.4 |
| L-MG | 0.0052 | 99.9 | 4.0 | 96.0 |

Note: T/C % (test/control) × 100 and I % = 100 − T/C % (where I % is the inhibition of tumor growth)

MG and L-MG were found to be potent in topical treatment. However, L-MG was found to be far more effective than MG in systemic treatment of tumors. By this method of physically latentiating methylglyoxal, an increased amount of alpha-ketoaldehyde was delivered to the tumor cells.

Pathological examination of tumor bearing mice treated with liposome encapsulated methylglyoxal (L-MG) shows an initial rapid increase of leukocytes in the circulating blood and in the tumor areas. This probably reflects an activation of the reticulo-endothelial system (RES) which results in the mass destruction of malignant cells. Reticula cells continue to accumulate and result in a rapid necrosis of cancerous cells. The appearance of a reactive granulation tissue replaces the cell debris. These phenomena are absent in non-tumorous control subjects.

L-MG treated tumor-bearing mice also have enlarged spleens due to the marked increase of hematopoietic activity, including an increased number of megakaryocytes and normoblasts within the bone marrow. Leukocyte formation was also occasionally observed in such secondary sites, as the liver and kidneys. However, the pancreas, skin and muscles appeared normal. In some cases, a violaceous and homogenous material was found within the tubules of the kidneys. This is probably due to the inadequate excretion of the metabolic products in patients with kidney failure. Administration of diuretics or mannitol may rectify this condition.

When additional sarcoma-180 cells were subsequently injected (s.c. or i.p.) into L-MG treated tumor-bearing mice these cells did not develop into observable tumors.

EXAMPLE 4

The Effect of CaRest-M3™ on Human Tumor Cell Lines

Materials and Methods

The National Cancer Institute panel consists of 60 human tumor cell lines, derived from seven cancer types (lung, colon, melanoma, renal, ovarian, brain, and leukemia), against which compounds are tested. Compounds are tested against human prostate tumor cell lines in a separate panel performed in an identical manner. The cell line growth medium has a stable physiological pH of 7.4 in atmospheric $CO_2$ and derives its buffering capacity from β-glycerophosphate. The medium is optimized by the addition of biotin, L-asparagine, pyruvate and oxaloacetate. The screen is designed to enhance the ability to discern differences in true cell killing (i.e., reduction in biomass) by using a relatively large cell inoculum (e.g., 20,000 cells/well) and a relatively short drug exposure/incubation time.

All tumor cell lines were inoculated into a series of standard 96-well microtitre plates on day 0 then preincubated for 24 hours. Test drugs, including the latentiated alpha-ketoaldehyde, CaRest-M3™, were then added in five tenfold dilutions starting from the highest soluble concentration, and incubated for a further 48 hours. Following this, the cells were fixed in situ, washed, and dried. A sulforhodamine B (SRB) protein assay was used to estimate cell viability or growth via microcomputers.

From each test, a series of dose-response curves (e.g., one curve, five concentration points for each cell line) is generated. A mean graph was generated which measured the relative cell line sensitivities to a given drug by comparing the relative drug concentrations required to produce the same level of response: growth inhibition-50 ($GI_{50}$), total growth inhibition (TGI), and lethal concentration-50 ($LC_{50}$).

CaRest-M3™ demonstrated both tumor growth inhibition and tumor cell killing against all the seven cancer types tested in a dose responsive manner. The results of the initial screen were verified by a subsequent screen, also performed at the National Cancer Institute, using identical conditions.

EXAMPLE 5

CaRest-M3™ Inhibition of the Colonization of B16 Melanoma Cells and Lewis Lung Carcinoma Cells Materials and Methods for the B16 Melanoma Cell Study Male C57BL/6 mice (VAF) were obtained from Taconic, Inc., (Germantown, N.Y.), and held in quarantine for a minimum of three days prior to the initiation of the study. Approximate weight of the mice was 17–20 grams at the time of inoculation.

B16 melanoma stocks (syngeneic with C57BL/6 mice) were passaged in vivo at 14-day intervals as subcutaneous solid tumors in VAF C57BL/6 mice. For each passage, several donor tumors were aseptically dissected from the animals and pooled. A 1:10 dilution brei was prepared by gently disrupting the tumor with Earles BSS (EBSS) in a Potter-Elvehjem teflon tissue homogenizer. An aliquot of 0.5 ml of the resulting tumor brei was injected subcutaneously into recipient mice. Aliquots of tumor were incubated in thiolglycollate broth to check for bacterial contamination.

Ten to fourteen days after implantation, B16 tumors were harvested, pooled, and incubated with agitation in trypsin/DNAase/EBSS at 37° C. for 10–15 minutes. Cells were washed by centrifugation, resuspended in fresh EBSS, and counted using Trypan Blue to determine the viable cell count. Approximately $10^5$ live B16 melanoma cells (0.2–0.5 ml) were injected intravenously via a caudal vein into C57BL/6 recipients. Aliquots of tumor were incubated in thiolglycollate broth to check for bacterial contamination.

Twenty-four hours after tumor implantation, mice were randomized into groups of 20. Test (three dose levels) and negative saline control solutions were administered intravenously (0.2 ml) once daily for ten consecutive days. Body weights were recorded on Days 1, 5, 10, and 20. On Day 20 ten mice from each group were sacrificed and their lungs were weighted and fixed in Bouin's fixative. A parallel set of control mice without tumor inoculation was included to provide baseline lung weights. The remaining mice were maintained for up to 60 days.

Materials and Methods for the Lewis Lung Carcinoma Cell Study

Female C57BL/6 mice were obtained from Taconic and held in quarantine for a minimum of three days prior to the initiation of the study. Approximate weight of the mice was 17–20 grams at the time of inoculation. Lewis lung carcinoma was maintained in vivo by serial subcutaneous passage in C57BL/6 mice. For each passage, several donor tumors were aseptically dissected from the animals and pooled. Ten to fourteen days after implantation, Lewis lung tumors were harvested, pooled, and incubated with agitation in trypsin/DNAase/EBSS at 37° C. for 10 minutes. Cells were washed by centrifugation, resuspended in fresh saline, counted using Trypan Blue and $10^5$ live Lewis lung carcinoma cells (0.2–0.5 ml) were injected intravenously via a caudal vein into C57BL/6 recipients. Aliquots of tumor were incubated in thioglycolate broth to check for bacterial contamination.

Twenty-four hours after tumor implantation, mice were randomized into groups of 20. Test (three dose levels) and negative control articles were administered intravenously (0.2 ml) once daily for ten consecutive days. Body weights were recorded on Days 1 and 5. On Day 26, one-half of the mice from each group were sacrificed and their lungs were weighted and fixed in formalin. A parallel set of control mice without tumor inoculation was included to provide baseline lung weights. The remaining mice were maintained for up to 50 days. On that day, remaining mice were killed by $CO_2$ asphyxiation and examined for gross evidence of tumor.

Criteria to evaluate the efficacy of the test article included the following:

1. Effect on survival time;
2. Effect on lung surface tumor colony counts;
3. Effect on tumor weight derived from lung weights of the animals sacrificed on Day 20 (B16 melanoma) or Day 26 (Lewis lung carcinoma).

Results

The results of the study are provided in tabular form below (Tables 2–6).

TABLE 2

B16 IV Metastasis Model - Survival Data

| COMPOUND | DOSE mg/kg/day | MEAN SURVIVAL TIME (Days) | % T/C | MEDIAN SURVIVAL TIME (Days) | % T/C |
|---|---|---|---|---|---|
| CaRest-M3 ™ | 1.5 | 24.1 | 121 | 24.5 | 117 |
| CaRest-M3 ™ | 3.0 | 27.2* | 137 | 27.0* | 129 |
| CaRest-M3 ™ | 6.0 | 30.8* | 155 | 31.5* | 150 |
| Saline control | — | 19.9 | 100 | 21.0 | 100 |

(*p $\leq$ 0.05 by t-test, Biologically significant activity: T/C $\geq$ 125%)

TABLE 3

B16 IV Metastasis Model - Lung Colony Counts

| COMPOUND | DOSE (mg/kg/day) | MEAN COLONY COUNT | % T/C |
|---|---|---|---|
| CaRest-M3 ™ | 1.5 | 66 | 78 |
| CaRest-M3 ™ | 3.0 | 57* | 67 |
| CaRest-M3 ™ | 6.0 | 40* | 47 |
| Saline | — | 85 | 100 |

(*p $\leq$ 0.05 by t-test)

TABLE 4

B16 IV Metastasis Model - Lung Tumor Weights

| COMPOUND | DOSE (mg/kg/day) | MEAN TUMOR WEIGHT | % T/C |
|---|---|---|---|
| CaRest-M3 ™ | 1.5 | 147 | 73 |
| CaRest-M3 ™ | 3.0 | 103* | 51 |
| CaRest-M3 ™ | 6.0 | 97* | 48 |
| Saline | — | 200 | 100 |

(*p $\leq$ 0.05 by t-test)

TABLE 5

Lewis Lung Carcinoma IV Metastasis Model - Survival Data

| COMPOUND | DOSE (mg/kg/day) | MEAN SURVIVAL TIME (Days) | % T/C | MEDIAN SURVIVAL TIME (Days) | % T/C | % TUMOR FREE SURVIVOR |
|---|---|---|---|---|---|---|
| CaRest-M3 ™ | 1.5 | >30.2 | >126 | 26.5 | 113 | 10 |
| CaRest-M3 ™ | 3.0 | >33.1* | >138 | 31.5 | 134 | 20 |
| CaRest-M3 ™ | 6.0 | >35.0* | >146 | 32.0 | 136 | 30 |
| Saline | — | 23.9 | — | 23.5 | — | 0 |

(Biologically significant activity: T/C $\geq$ 125%; *p < 0.05)

TABLE 6

Lewis Lung Carcinoma IV Metastasis Model - Mean Lung Tumor weights and Colony Counts

| COMPOUND | DOSE (mg/kg/day) | MEAN TUMOR WEIGHT % T/C | MEAN COLONY COUNT % T/C |
|---|---|---|---|
| CaRest-M3 ™ | 1.5 | 19* | 39 |
| CaRest-M3 ™ | 3.0 | 15* | 20* |
| CaRest-M3 ™ | 6.0 | 21* | 21* |

(*p < 0.05)

EXAMPLE 6

CaRest-M3™ Inhibition of Growth of Ehrlich Ascites Carcinoma in Mice

Materials and Methods

Twenty CFLP female mice were inoculated intraperitoneally with 15 million Ehrlich ascites carcinoma cells in 0.5 ml of ascites fluid. The mice were randomly divided into two groups of 10 mice/group. The control group received 1 ml of 0.9% NaCl solution. The second group was treated with 1 ml of the test compound. The route of administration was intraperitoneal injection, once daily for ten consecutive days. Body mass and mortality were recorded daily. After ten days of treatment the animals were sacrificed. The ascites fluid volume and ascites cell count were determined. The effect was expressed as inhibition of tumor cells in the treated group in relation to the control group. Statistical analysis was performed using a standard t-test.

Results

Figure 7:
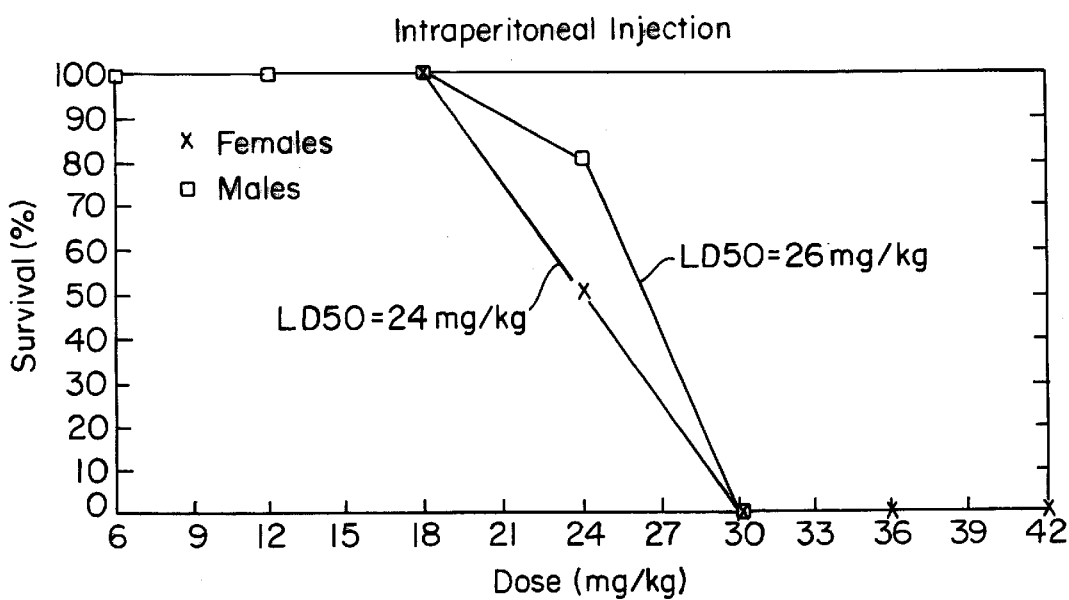
FIG. 7 is a graphic representation of the results of the acute toxicity study with CaRest-M3 in mice by intraperitoneal injection.

There was no mortality in either of the test groups. As shown in FIG. 7, the test compound (CaRest-M3™) completely cured 70% (7/10) of the test animals. There was no similar response among the control animals. In the 3 mice that were not cured, there was a 25% reduction in ascites fluid volume and a 49% reduction in ascites fluid cell count compared to the control group. Overall, the group treated with the test compound showed a 77% reduction in ascites fluid volume (% T/C; 23; p-value<0.01) and an 85% reduction in ascites fluid cell count (% T/C: 15; p-value$\leq$0.05) compared to the control group.

EXAMPLE 7

Study of CaRest-M3™ in Dogs with Malignancies

Study Protocol

Dogs Eligible

Dogs with measurable, biopsy proven malignant melanomas, squamous cell carcinomas and mammary carcinomas were eligible for treatment with informed consent of their owners. Tumors should be less than 2 cm in widest diameter and larger tumors can be reduced to this size surgically. Candidates had a predicted life expectancy of at least three weeks, and a White Blood Cell count within normal limits. Those that had received chemotherapy or radiation treatment were not included. Owners had to be willing to return for post treatment follow-up examination.

Pretreatment Evaluation

Pretreatment evaluation included physical examination, tumor biopsy, tumor measurement and photographs, complete blood count (CBC) with differential, urinalysis, chemistry profile, and radiographic metastatic evaluation (three views) of the thorax. Additional testing such as ultrasound examination may be indicated for clinical staging in some cases.

Treatment

The CaRest-M3™ agent was provided in a 0.30 mg/ml sterile solution diluted 50% (2:1 dilution) with sterile 0.9% saline for intravenous injection. The solution was supplied in a multi-dose vial and was refrigerated. The drug was given at an initial dose of 0.3 mg/kg (2 ml/kg of the diluted solution) and administered intravenously over a 5 minute period by means of an indwelling butterfly needle. The same dose was repeated daily for a minimum of fourteen (14) consecutive days. The vein in which the injection was given was recorded, with the first four injections given in the right and left cephalic, and right and left saphenous veins, and the remaining injections rotated similarly. If any localized swelling or phlebitis was noted, the injection time was increased to 15 minutes. Treatments were given on an outpatient basis if the owner could return on a daily basis, otherwise the dog was hospitalized. The owner was asked to observe the dog for any urinary problems.

Data Collection During Treatment

Performance scores were recorded daily, as well as any adverse effects. Daily observations and notes regarding tumor size, degree of inflammation, hardness and presence of exudate were recorded. If there was no change from the previous day this was also noted. Complete blood count with differential was taken on Day 1 and then every other day as long as the treatment continued (i.e., days 3, 5, 7, 9, 11, 13, 15, 17, 19). Photographs of the tumor were taken on Days 1, 6, 11 and the last day of treatment; photographs were taken at other time if there was a marked change in the tumor's appearance. On the eleventh day of treatment (Day 11), the dogs had a complete physical examination, tumor biopsy using the same biopsy methodology as in the pretreatment evaluation, tumor measurement and photographs, complete blood count (CBC) with differential, urinalysis, chemistry profile, and radiographic metastatic evaluation of the thorax (if indicated).

Length of Treatment

The length of the treatment was based on the results in the Day 11 biopsy and evaluation. If all tumor cells were necrotic on the Day 11 biopsy section, then the total treatment duration was fourteen (14) days. If there were viable tumor cells in the Day 11 biopsy section, then the total treatment duration was twenty (20) days.

Follow-Up Examination

The next full examination was ten days after the last full day of treatment (i.e., either Day 24 or Day 30). The exam included tumor measurements, CBC with differential, profile, selenium, urinalysis, photographs and radiographic metastatic evaluation of the thorax (if indicated). After treatment, dogs with evidence of tumor regression were seen monthly for six months or until progression of tumor was evident. A second cycle of treatment can be given if there was a significant reduction of tumor and if the tumor reoccurred or increased within six months of the end of the first treatment. Monitoring for the second cycle would be the same as for the first. Complete gross and microscopic necropsies were done on animals that die or are euthanized during that time.

Results

Summary of pilot clinical studies in dogs with spontaneous tumors on five dogs that have undergone treatment and are at least two months into the follow-up period. Dogs 2–5 underwent 20 consecutive days of treatment as outlined in the attached protocol. On average, the response to treatment was delayed 2—3 months post-treatment with CaRest-M3™.

Dog 1—Presented with metastatic squamous cell carcinoma of the oral cavity with invasion of the upper jaw bone. The dog has remained in complete remission 10 months post-treatment. X-ray studies have shown that the previous metastatic lytic lesions in the bone are remodelling with new bony formation.

Dog 2—Presented with malignant melanoma of the hind leg, metastatic to the lymph nodes. The dog was showing 20–30% primary tumor regression with no new metastatic sites 6 months post-treatment.

Dog 3—Presented with metastatic malignant melanoma of the oral cavity. The dog was showing 95% tumor regression 3 months post-treatment.

Dog. 4—Presented with metastatic malignant melanoma of the oral cavity. The dog had tumor reoccurrence in the first month and was euthanized by the owners.

Dog 5—Presented with metastatic malignant melanoma of the oral cavity. The dog is showing no progression of tumor (stable disease) 2 months post-treatment.

EXAMPLE 8

Inhibition of B16F10 Melanoma Tumor Cell Migration and Cell Adhesion

Invasion/Chemotaxis Assay

1.) Each condition should be done in duplicate or triplicate (i.e., 2 or 3 filters per condition).
2.) Use PVPF 13 um filters with 8 um pore size, place shiny-side down on a sterile tissue culture plate, and label with a black ball point pen on the edge of each filter.
3.) Dilute cold 10 mg/ml Matrigel in ice-cold ddH$_2$O, usually at 1:10, 1:15, and 1:20. Dilute type IV collagen (approximately 0.8 mg/ml) 1:8 in cold 0.1% acetic acid. Vortex all solutions well and keep on ice during use.
4.) Apply 50 $\mu$l of each solution to the center of each filter. Make a key of which filter is coated with which protein solution.
5.) Allow to dry overnight in a hood (uncovered).

The day of the Experiment

6.) Wash cells with CMF-PBS, and lift them with Versene. Spin the cells down and resuspend in DMEM/0.1% BSA and count them. Repellet the cells and resuspend in DMEM/0.1% BSA such that there are 1 million cells/ml media (need 200,000 B16F10 cells per chamber).
7.) Load the bottom chamber with 200 $\mu$l of varying concentrations of CaRest-M3™ and serum-free media (DMEM).
8.) Layer the coated filter on the bubble of solution (coated side up). Avoid introducing any bubbles between the solution and the filter.
9.) Screw in the chamber screw tightly.
10.) Add 200 $\mu$l of the cell suspension (200,000 cells/chamber) to each Bovden chamber.
11.) Top each chamber with 650 u. of DMEM/0.1% BSA, filling the chamber.
12.) Place the chambers in an incubator for 5 hours.
13.) Pour off cells, unscrew chambers, and carefully remove filters with forceps. Place bottom side up on wax plate and pin in place (at the edge).
14.) Fix cells quickly with Diff-Quick fixative (methanol based). Pour off.
15.) Quickly stain with the Diff-Quick red stain, pour off, then the blue stain, and pour off.
16.) Add water to the wax dish, swirl, and pour off.
17.) Dip each filter in water then place each filter onto a glass slide, bottom-side-down (so invert). Wipe off cells on the top side of the filter with cotton swabs. Put a drop of Permount on each filter when fairly dry and coverslip.
18.) Results can be quantified on an Optimax computerized imaging system. Cells may also be counted manually to determine which have migrated through the filter.

CELL ADHESION ASSAY

The cell adhesion assay using B16F10 melanoma cells can be performed in 96, 48 or 24 well microtiter plates. Respective volumes are indicated as follows:

| 96 WELL | 48 WELL | 24 WELL |
|---|---|---|
| 1.) 100 $\mu$L MEM | 250 $\mu$L MEM | 340 $\mu$L MEM |
| 2.) ADD LAMININ (2 MG/ML IN MEM) | | |
| 5.5 $\mu$G | 10 $\mu$G | 13.6 $\mu$G |
| 27.4 $\mu$G | 50 $\mu$G | 68.2 $\mu$G |
| 54.5 $\mu$G | 100 $\mu$G | 136.0 $\mu$G |
| 3.) SWING FOR 2 MIN. | | |
| 4.) PUT IN CO$_2$ INCUBATOR FOR 2 HRS | | |
| 5.) ADD 100 $\mu$L MEM + 3% BSA | 250 $\mu$L | 340 $\mu$L |
| 6.) PUT IN CO$_2$ INCUBATOR FOR 30 MIN–1 HR. | | |

-continued

| 96 WELL | 48 WELL | 24 WELL |
|---|---|---|
| 7.) REMOVE ALL MEDIA (BY ASPIRATION) | | |
| 8.) ADD 100 μL OF MEM + 0.02% BSA | 400 μL | 680 μL |
| 9.) ADD 40,000 CELL/WELL WITH VARYING MOLAR CONCENTRATIONS OF CaRest (TEST COMPOUND) | 80,000 CELL/WELL | 100,000 CELL/WELL |
| 10.) PUT IN $CO_2$ INCUBATOR FOR 1 HR. | | |
| 11.) REMOVE ALL MEDIA (ASPIRATION) | | |
| 12.) WASH WITH PBS 2X | | |
| 13.) ADD 200 μL OF TRYPSIN | 500 μL | 500 μL |
| 14.) ADD 9.8 ML ISOTONE | | |
| 15.) COUNT CELLS IN COULTER COUNTER | | |

Results are shown in Table 7 (CaRest-M3™ Migration Study) and Table 8 (CaRest-M3™ Adhesion Study).

TABLE 7

Inhibition of B16 Melanoma Tumor Cell Migration by CaRest-M3

| Dilution-fold | Grams CaRest-M3 per 200 microliter | Micrograms per 200 microliter | Molarity | Mean area |
|---|---|---|---|---|
| 10000 | 3.0E-07 | 0.3 | 8.9E-06 | 210000 |
| 3000 | 1.0E-06 | 1 | 3.0E-05 | 235000 |
| 1000 | 3.0E-06 | 3 | 8.9E-05 | 225000 |
| 300 | 1.0E-05 | 10 | 3.0E-04 | 0 |
| 100 | 3.0E-05 | 30 | 8.9E-04 | 0 |

TABLE 8

Inhibition of B16 Melanoma Tumor Cell Adhesion by CaRest-M3

| Dilution-Fold | Grams CaRest-M3 per milliliter | Micrograms per milliliter | Molarity | Effect |
|---|---|---|---|---|
| 10000 | 3.0E-07 | 0.3 | 1.8E-06 | − |
| 3000 | 1.0E-06 | 1 | 5.9E-06 | ++ |
| 1000 | 3.0E-06 | 3 | 1.8E-05 | ++ |
| 300 | 1.0E-05 | 10 | 5.9E-05 | +++ |
| 100 | 3.0E-05 | 30 | 1.8E-04 | ++++ |

− no effect
++ some cells adhere
+++ some cells adhere
++++ no cells adhere

EXAMPLE 9

Preventing Pregnancy in Mice by Administering Latentiated Alpha-ketoaldehyde

Six 5 month old female CD1 mice were injected intraperitoneally with N-1-[hydroxyacetonyl]maleimide for 12 days (2.5 mg/kg/day in 0.9% saline). Another group of the same mice were injected intraperitoneally with 0.9% saline for 12 days. This second group of mice served as the control. Two experienced males were introduced to each group of females and kept together for 8 days during which time the females received their daily injection.

Normal values (approximate):

| Gestation | 19–21 days |
|---|---|
| Estrus duration | 2.5 days |
| Trophoblast formation | 4–5 days |
| Implantation | 4–6 days |

Copulation plugs were seen on each female by the 12th day of injection, and signs of pregnancy were seen on the control females on the 15–16th day of the experiment. The females delivered on 20–23rd (control) and 24–27th (treated) day respectively. The results are shown in Table 9 below.

TABLE 9

| | Control 12 female | Test 12 female |
|---|---|---|
| # of pups delivered | 106 (12 females) | 11 (2 females) |
| T/C % | 100 | 10.3 |
| I % | 0 | 89.7 | male/female ratio of the pups: 45% male, 55% female

The experiment was repeated with the same females two months later, except that females of the control group were assigned to the test group, while females of the test group were reassigned to the control group. The result of the second experiment showed 83.3% inhibition of delivery by the treated females. The control group delivered 102 pups (T/C=100%).

These results demonstrate that latentiated methylglyoxal inhibits implantation of fertilized mouse eggs. Two mice delivered a reduced size litter. These females probably had a delayed ovulation, which is quite common among mice. The treatment had no effect on the reproductive cycle of the females.

EXAMPLE 10

Effect of CaRest-M3™ on Spermatozoa Stability

Freshly ejaculated human spermatozoa were washed once in Buffered Saline Solution (BSS) at pH 7.2 and resuspended in the same solution or in a solution containing BSS+6 mM EDTA. CaRest-M3™0 was diluted in BSS 10, 30 and 100 times, respectively. The spermatozoa were incubated in the MB-BSS or MB-BSS-EDTA mixture for one hour. Then SDS or SDS-EDTA was added. The swelling was stopped by glutaraldehyde after 30 min. The spermatozoa were assessed in phase contrast microscopy (1250×magnification).

The "points" is an index and calculated from % II (moderately swollen heads)+2*% III (grossly swollen heads). 97% stable (=I) and 3 points means that there were only 3% having moderately swollen heads. (For example, if 1% had grossly swollen heads, the points were 2+1*2=4). With this index highly, swollen sperm heads are given more "weight". The data in Table 10 (results from 2 experiments) show that CaRest-M3™ causes a hyperstabilization of the sperm chromatin.

TABLE 10

| | SDS 1% pH 9 SDS treat. Stable | Points | EDTA % = 6 mM SDS-EDTA Stable | pH 7.2 Points |
|---|---|---|---|---|
| Exper. 1 | | | | |
| BSS | | | | |
| Control | 91 | 11 | 74 | 33 |
| Dilut. 1:100 | 94 | 6 | 74 | 42 |
| 1:30 | 97 | 3 | 80 | 23 |
| 1:10 | 97 | 3 | 99 | 1 |
| BSS + EDTA | | | | |
| Control | 66 | 52 | 73 | 41 |
| Dilut. 1:100 | 70 | 44 | 69 | 42 |
| 1:10 | 97 | 5 | 99 | 1 |
| Exper. 2 | | | | |
| BSS | | | | |
| Control | 84 | 17 | 58 | 57 |
| Dilut. 1:100 | 86 | 18 | 69 | 48 |
| 1:30 | 93 | 7 | 86 | 18 |
| 1:10 | 90 | 10 | 93 | 9 |
| BSS + EDTA | | | | |
| Control | 63 | 57 | 64 | 54 |
| Dilut. 1:100 | 64 | 51 | 66 | 48 |
| 1:30 | 90 | 13 | 90 | 12 |
| 1:10 | 90 | 11 | 91 | 10 |
| Mean Values | | | | |
| BSS | | | | |
| Control | 87.5 | 14 | 66 | 45 |
| Dilut. 1:100 | 90 | 12 | 71.5 | 45 |
| 1:30 | 95 | 5 | 83 | 20.5 |
| 1:10 | 93.5 | 6.5 | 96 | 5 |
| BSS + EDTA | | | | |
| Control | 64.5 | 54.5 | 68.5 | 47.5 |
| Spadn 1:100 | 67 | 47.5 | 67.5 | 45 |
| 1:30 | 86 | 18 | 86.5 | 17 |
| 1:10 | 93.5 | 8 | 95 | 5.5 |

EXAMPLE 11

Radiation Enhancement

Thiol containing compounds protect cells against ionizing radiation damage. Moreover, the sensitivity of bacteria and mammalian cells towards gamma irradiation can be significantly increased by decreasing their thiol content. (Ashwood-Smith, *J. Radiat. Biol.*, 15:285 (1969)). Therefore, compounds that reduce the free —SH content of cells make them more susceptible to radiation damage.

Mice carrying ascitic Sarcoma-180 cells (20 million) were injected with methylglyoxal (120 mg/kg mouse). Ten minutes after the injection the mice were irradiated with a gamma source (612 RAD equivalent of 400 R total body radiation; calculated lethal dose: LD-50/30 days). The treatment was repeated 3 times 4 days apart. Positive controls were subjected to treatment with methylglyoxal or radiation alone. One day after the last radiation, the animals were sacrificed, the ascitic fluid was collected and the malignant cells were counted. Results are shown in Table 11.

TABLE 11

| | T/C % | I % | P % |
|---|---|---|---|
| control | 100 | 0 | 0 |
| MG (alone) | 104.7 | na | 4.7 |
| RAD (alone) | 36.9 | 36.8 | na |
| RAD + MG | 7.7 | 92.3 | na |

RAD = Radiation
MG = Methylglyoxal
P % = Promotion
I % = Inhibition

EXAMPLE 12

Latentiated Alpha-Ketoaldehydes Inhibit the Rejection of Skin Grafts

The experiments described here were performed on random bred Swiss albino mice (white, females, average body weight 26±3 g; Charles River CD-1 strain) and inbred C3HStCrl mice (cinnamon gray, females, average body weight 10°2 grams; Charles River pedigreed breeders from L. C. Strong Foundation) and orthotopic skin transplants were made in both ways, that is, white to gray and gray to white.

Standard transplantation technique (Billingham, R. E. and Silvers, W. K., TRANSPLANTATION OF TISSUES AND CELLS, The Wistar Institute Press, Philadelphia, p. 8, (1961)) was utilized. Briefly, from nembutal-anesthetized animals, 4–6 "pinch" grafts (full thickness, 34 mm in diameter) of the close clipped and sterilized skin were collected from the thorax and immediately transplanted. The grafts were positioned in the "beds" (in place of the pinch-graft) and were held in position by tulle gras (vaseline-impregnated gauze) and by plaster-of-Paris impregnated bandage around the thorax. The bandages were removed on the 69th day after the transplantation and the future development of the grafts was followed by macroscopical observations.

Positive and negative controls were made simultaneously for skin rejection:

1. Four positive control isografts (white to white, and gray to gray) were made. These grafts showed a confluence and union of the fitted grafts with the surrounding skin and beds in 7–10 days. On the 21–28th day the fur-bearing skin had regenerated a completely new crop of hairs indistinguishable from the original population with respect to color, density and orientation.

2. Four negative control heterografts (white to gray and gray to white) were made without treatment. No confluence and union with the surrounding tissue which was locally inflamed was observed. On the 10–12th day after transplantation, intravascular thrombi, capillary ruptures, extravasation of blood were observed, the first signs of necrosis and rejection of the grafts occurred on the 18–25th day.

The heterografts with treatment followed three courses with chemically latentiated methylglyoxal (at dose level 3.74 mg/kg/animal/day) administered intraperitoneally in a total amount of 1.0 ml/animal/day.

a. Animals were treated for 10 days with the test compound before grafts were exchanged and treatment was discontinued on the day of transplantation.

b. Animals were not treated before the grafts were exchanged but the treatment started on the day of transplantation and continued for 10 days.

c. Animals were treated for 10 days with the test compound before the grafts were exchanged and the treatment schedule was continued for 25 days after the transplantation.

TABLE 12

| Assay | Mice | Type of Graft* | Treatment + | Result (NOTE: % figures in results are cumulative values) |
|---|---|---|---|---|
| Positive | 10 | w to w | no | 100% take in 21–28 days |
| control | 10 | g to g | no | 100% take in 21–28 days |
| Negative | 10 | w to g | no | 100% rejection in 10–25 days |
| control (a) | 10 | g to w | no | 100% rejection in 10–25 days |
| Pretreat. | 10 | w to g | yes | 30% rejection in 26–30 days |
| for 10 days (b) | 10 | g to w | yes | 100% rejection in 31–40 days |
| Post graft | 10 | w to g | yes | 10% rejection in 26–31 days |
| treatment for 10 days (c) | 10 | g to w | yes | 10% rejection in 31–40 days |
| Pretreatment | 20 | w to g | yes | No rejection in 26–30 days |
| for 10 days and post graft treatment for 25 days | 20 | g to w | yes | 10% rejection in 31–40 days |

+ Treatment: daily injection with 3.74 mg/kg methylglyoxal-maleimide in 1.0 ml saline by intraperitoneal route/mouse/day
*The w stands for white mice (Swiss albino, random bred, Charles River CD-strain. The g stands for cinnamon gray mice (C3HStCrt, inbred strain)

EXAMPLE 13

Effect of Alpha-Ketoaldehyde on the Proliferation of Molds (Fungi) in Vitro (1) Stock solutions is 26% 2-propanediol:

| | | |
|---|---|---|
| Methylglyoxal (MG) | (MW = 72.06) | 0.958 M |
| Chloromethylglyoxal (CMG) | (MW = 106.51) | 0.995 M |
| Dichloromethylglyoxal (DCMG) | (MW = 140.45) | 0.854 M |

(2) Microorganisms:

*Penicillium notatum*
*Aspergillus niger*

(3) Assay: The microorganisms were grown in Saburaund's dextrose agar at 35° C. for stock cultures. For the assay the spores were plated on Mueller-Hinton agar plates (7 cm dia). The test compounds were applied to the plates on sensi disks (6 mm dia, Whatmann #17 paper) in volumes of 10, 20, 30, 40 microliters made up to 40 plating volume of microliters with the solvent. The plates were incubated at room temperature and in the dark for 40 hrs. The diameter of the inhibition ring around the sensi disks were measured. The results are shown in Table 13.

TABLE 13

| | 10 | 20 | 30 | 40 |
|---|---|---|---|---|
| | \multicolumn{4}{c}{microliters of alpha-ketoaldehyde mm inhibition diameter} | | | |
| Penicillium | | | | |
| MG | — | — | 8 | 10 |
| CMG | 8 | 10 | 12 | 14 |
| DCMG | 8 | 10 | 13 | 16 |
| | 10 | 20 | 20 | 40 |
| | \multicolumn{4}{c}{microliters of alpha-ketoaldehyde mm inhibition diameter} | | | |

TABLE 13-continued

| Aspergillus | | | | |
|---|---|---|---|---|
| MG | — | — | 7 | 9 |
| CMG | 8 | 11 | 17 | 22 |
| DCMG | 10 | 12 | 14 | 15 |

With penicillium: strong growth, sharp edged, clear inhibition zones. With aspergillus: strong growth, somewhat "fuzzy" edged, clear inhibition zones.

The inhibition rings with CMG and DCMG remained unchanged in the highest concentration for 8 days. By this time the penicillium plate developed a second ring around the inhibited area: a white zone averaging 10–15 mm in diameter. Under the microscope, it was seen that the spore formation in this area was inhibited while mycelium development was not. Since the rest of the plate was colored dull green indicating spores are present, the mycelium and spore development of this fungus show different sensitivity towards methylglyoxal (MG).

EXAMPLE 14

Effect of Alpha-Ketoaldehyde on the Proliferation of *Candida albicans*

The *Candida albicans* used for this experiment was obtained from Dr. Scott, Hoffmann La Roche.

(A) Sensitivity of *C. albicans*

1. Stock Solutions

Stock solutions of the following test compounds were dissolved in 0.9% saline. However DOV was dissolved in water.

| μmole/10 μl | | |
|---|---|---|
| MG | 2.22 | methylglyoxal |
| CMG | 1.09 | chloromethylglyoxal |
| DCMG | 1.11 | 3,3 dichloromethylglyoxal |
| AcMG | 12.70 | 3-acetyl methylglyoxal |
| MGMALI | 0.96 | N-1-[hydroxyacetonyl]maleimide |
| KE | 4.30 | kethoxal |
| DOV | 4.80 | 2,4-dioxovaleric acid |
| MALI | 0.94 | maleimide |
| PhG | 0.10 | phenylglyoxal (limit solubility) |
| 5FC | 0.43 | 5-fluorocytosine |
| AMPB | 0.96 | amphotericin-B |

2. Sensitivity Assay:

*C. albicans* isolated from clinical specimens was densely grown in Sabouraund broth at 35° C. A loopful of yeast suspension was evenly spread on the surface of Mueller-Hinton agar plates (7 cm diameter) with a sterile cotton applicator and incubated for 12 hours. The test compounds were placed on the surface of the sensidisks (Whatmann No. 17 paper, 6 mm diameter) in a volume of 5, 10, 20, and 50 μl of stock solutions and made up a final volume of 50 μl with saline. The plates were incubated at 37° C. for 24 hours (*) and 48 hours (**) when the diameters of the inhibitory rings were recorded. Photographs were also taken of plates. Results are shown in Table 14.

TABLE 14

| | | μ liters of test compound | | | |
|---|---|---|---|---|---|
| | | 5 | 10 | 20 | 50 |
| | | mm inhibition diameters | | | |
| MG | * | — | — | 8 | 10 |
| | ** | — | — | — | — |
| CMG | * | — | 7 | 21 | 33 |
| | ** | — | — | 10 | 31 |
| DCMG | * | — | 8 | 20 | 32 |
| | ** | — | — | 17 | 29 |
| AcMG | * | — | 18 | 31 | 34 |
| | ** | — | 11 | 24 | 30 |
| MALI | * | — | 8 | 18 | 22 |
| MG | ** | — | — | 17 | 22 |
| KE | * | — | 7 | 17 | 25 |
| | ** | — | — | 16 | 24 |
| DOV | * | negligible | | | |
| MALI | * | 13 | 21 | 29 | 30 |
| | ** | — | 17 | 25 | 30 |
| PhG | * | — | — | 5 | 8 |
| | ** | — | — | — | — |
| MALI CMG | ** | 29 | 34 | 40 | 42 |
| MALI DCMG | ** | 37 | 32 | 38 | 40 |
| 5FC | * | 33 | 45 | 50 | 55 |
| AMP-B | * | — | — | 2 | 5 |

(B) Inhibition of *C. albicans*

1. Stock Solutions

Same as above.

2. Activity Assay

Stock cultured *C. albicans* is used. The yeast isolated from clinical specimens was stock cultured (subcultured) on semisolid trypsoy agar plates. A loopful of microorganism was transferred to Sabouraund broth (SRB, 5 ml) and the rate of growth was observed for 12, 24, and 48 hours at 36° C. Comparable growth rate was observed with subcultures at any incubation time. Thus, from the subculture(s), transfers were made every 48 hrs into SRB to keep the experimental strain available for assays. From the 24–48 hrs SRB cultures a loopful of turbid solutions was transferred and spread on either (a) trypsoy agar plates or (b) EBM agar plates which were fortified with horse and calf serum and incubated at 36° C. for 24–48 hrs.

Plate culture on (a) showed strong growth in 24 hrs while plate (b) supported only slight growth even at 48 hrs. Plate (a) was selected for growth inhibition assay(s) with ketoaldehydes.

One milliliter of SRB culture (24–48 hrs growth) was mixed with 10 ml trypsoy agar, warmed to 38° C. and rapidly poured into sterile Petri dishes (7 cm), spread evenly and allowed to solidify. The selected test compounds (in 30 ul total volume, as above) were placed in sensidisks (6 mm dia., Whatman #17) on the infected agar surface. The plates were incubated for 24 hrs at 37° C. The extent of inhibition, clear zones around the sensi disks, were measured and recorded. In some cases contact photorecords were also made with the plates.

These assays were aimed at finding the variations of inhibition due to (i) the variable amount of yeast and (ii) a three dimensional area of the plates. Each result is the statistical mean of twenty assays on different batches of *C. albicans*.

| | mm Inhibition Diameters (30 μl test, 24 hrs incubation) mean ± standard deviation (SD) | |
|---|---|---|
| MG | 6.0 | 2.0 |
| CMG | 26.6 | 4.5 |
| DCMG | 23.0 | 4.1 |
| AcMG | 25.3 | 7.1 |

With heavy inoculum, the inhibition effects are evident in 24 hrs. With the light inoculum, although inhibition showed very litte or no "regrowth" (transient inhibition), the relatively slow growth of *C. albicans* required an extension of incubation time to up to 4 days.

EXAMPLE 15

The Effects of Alpha-Ketoaldehydes on Blood Coagulation (1). Assay:

200 microliter thromboplastin (Ortho) was mixed with 10 microliter of alpha-ketoaldehyde (KA) stock solution. 100 microliters of citrated human blood plasma was added and the clot formation time (in seconds) was measured on a Fibrinometer. The effect of the alpha-ketoaldehyde on coagulation time was evaluated by comparing the clotting time of the KA treated plasma with the untreated control. The result (d%) was read from a special chart expressing the clotting activity. All measurements were run in triplicate 37° C. (waterbath) in special tubes. All solutions were prewarmed.

| (2). KS Stock Solutions: - in 0.9% Saline | |
|---|---|
| methylglyoxal (MG) | 0.988 M |
| chloromethylglyoxal (CMG) | 0.940 M |
| 3,3-dichloromethylglyoxal (DCMG) | 0.551 M |
| 3-acetylmethylglyoxal (AcMG) | 0.890 M |
| Phenylglyoxal (PhG) | 0.694 M |
| 3-Phenylmethylglyoxal (PMG) | 0.856 M |

(3). Results (A) The plasminogen and ketoaldehyde were kept for 1–2 seconds before the blood plasma was added. Results are shown in Table 15.

TABLE 15

|  | Coagulation Time (sec) | Clotting (d %) | Nature of Clot |
|---|---|---|---|
| control | 24 | 22 | hard |
| MG | 25 | 20 | hard |
| CMG | >200 | infinite | no |
| DCMG | >200 | infinite | no |
| AcMG | 21.5 | 28 | hard |
| PMG | 36 | 10.5 | hard |
| PhG | 35 | 11 | hard |

(B) The plasminogen and KA were incubated for varying times before the blood plasma was added ((a) abnormal plasma in Table 16; (b) normal plasma in Table 17; (c) whole blood in Table 18).

(a) With plasma from a patient with prothrombin time of 26 sec, d% - 19. The Normal (healthy) blood plasma clotting time is 10–12 sec d% - 100. Results are shown in Table 16 below.

TABLE 16

|  | Incubation Time (sec) | Clotting Time (sec) | Clotting (d %) |
|---|---|---|---|
| MG | 30 | 39.0 | 15 |
|  | 60 | 32.0 | 13 |
|  | 130 | 39.0 | <10 |
|  | 190 | 41.0 | <10 |
|  | 300 | 91.8 | <10 |

(b) with normal plasma: clotting time—11.7 sec, d%=100. Results are shown below in Table 17.

TABLE 16

|  | Incubation Time (sec) | Clotting Time (sec) | Clotting (d %) |
|---|---|---|---|
| MG | 5 | 12.9 | 96 |
|  | 60 | 14.9 | 55 |
|  | 129 | 15.4 | 53 |
|  | 240 | 19.0 | 35 |
|  | 360 | 26.9 | 26 |
|  | 600 | >167.0 |  |
| CMG | 15 | 19.4 | 33 |
|  | 100 | >178.0 |  |
| 10X diluted | 10 | 13.5 | 37 |
| DCMG | 15 | >170.0 |  |
| 10x diluted | 10 | 12.9 | 96 |
| 20x diluted | 30 | 20.0 | 15 |
| AcMG | 120 | 13.9 | 78 |
| PhG | 120 | 19.5 | 33 |
| PMG | 120 | 21.2 | 28 |
| Control | (end of assay) |  |  |

(c) A trial assay where blood plasma was replaced with whole blood (control=14.9 sec, d%=100). Results are shown in Table 18.

TABLE 18

|  | Incubation Time | Clotting Time (sec) |
|---|---|---|
| MG | 70 | 16.5 |
|  | 150 | 19.4 |
|  | 180 | 20.0 |

TABLE 18-continued

| Incubation Time | Clotting Time (sec) |
|---|---|
| 240 | 22.0 |
| 360 | 24.0 |

EXAMPLE 16

Inhibition of Tissue Transglutaminase by Methylglyoxal

Materials and Methods

The ability of an α-ketoaldehyde, methylglyoxal, to inhibit tissue transglutaminase (TGase) was studied. Methylglyoxal was found to irreversibly inhibit the activity of TGase at concentrations as low as 10 nmol.

Guinea pig liver transglutaminase (TGase) was used for the assay. The test compound was methylglyoxal serially diluted with 0.15% NaCl. The conntrol compound was 0.9% saline diluted with 0.15% NaCl. The assay followed the published methods of Folk (Folk, J. E. et al. *Transglutaminases*, Methods in Enzymology, Ed.: A. Meister, vol. 113, pp. 358–367, New York: Academic Press, 1985).

The assay solution was prepared as follows: to 0.45 ml aliquots of 0.1M tris-acetate buffer (pH 7.5) were added 1 mM EDTA, 10 mM $CaCl_2$, 5 mM dithiothreitol, 1% succinylated Hammerstein casein and 0.5 $\mu$Ci [$^{14}$C]putrescine (100 Ci/M).

The reaction solutions was prepared as follows: 50 $\mu$l portions of samples containing 5 $\mu$l of tris-acetate buffer 1.0M (pH 8.0), 5 $\mu$l of 0.1M $CaCl_2$ as an activator, 10 $\mu$l of TGase (equivalent to 0.2 nmol) and varying dilutions of the test compound (methylglyoxal) or the control compound were incubated at 37° C. for 30 minutes.

To perform the test, 10 $\mu$l aliquots of the various reaction solutions were added to 450 $\mu$l of assay solution and reacted for 60 minutes at 37° C. The reaction was then stopped with the addition of 5 ml of 5% cold trichloracetic acid (TCA). The precipitates were washed with cold 5% TCA and collected on glass filters (Whatman GF/A) and the radioactivity of the samples was measured to determine % activity of the TGase in the samples. Results are expressed in CPM, % activity of TGase in the sample after addition of test/control compound and % inhibition of TGase activity after addition of test/control compound. Results are shown in Table 19.

TABLE 19

|  | CPM | % Acitivity | % Inhibition |
|---|---|---|---|
| reaction blank without enzyme: | 760 |  |  |
| reaction control without addition test/control compound | 250,200 | 100 |  |
| 10 nmol of control compound | no change | 100 | 0 |
| 20 nmol of control compound | no change | 100 | 0 |
| 30 nmol of control compound | no change | 100 | 0 |
| 10 nmol of methylglyoxal | 12,230 | 4.9 | 95.1 |
| 20 nmol of methylglyoxal | 9,500 | 3.8 | 95.2 |
| 30 nmol of methylglyoxal | 8,030 | 3.2 | 96.8 |

Each value is the average of triplicate assays.

EXAMPLE 17

In Vitro Anti-Parasitic Activity of CaRest-M3™

The ability of CaRest-M3™ (methylglyoxal-maleimide) to inhibit the viability of microfilariae or adult worms of

*Brugia Malayi* was tested. Microfilariae or adult worms of the species *Brugia Malayi* were incubated in a culture medium containing Dulbecco's Modified Eagle Medium, (DMEM) calf's serum and various concentrations of CaRest-M3™ (test) or 0.9% saline (control). The test was performed at 37° C. and 5% $CO_2$ atmosphere. Efficacy was determined by the ability of the compound to inhibit the mobility of the worms. CaRest-M3™ was found to be toxic to this parasite in vitro at concentrations as low as 0.1 mM. Results are shown in Table 20 for microfilariae and in Table 21 for adult worms.

tity of exudate and fibrin in the abdominal cavity, the organs were fibrinously interlaced and covered by fibrin.

Materials & Methods: The doses chosen for the 42-day subacute study were 0.25 mg/kg, 0.5 mg/kg and 1.0 mg/kg. 104 Wistar rats were divided into four groups. The control group and group III had 16 males and 16 females each; groups I and II had 10 males and 10 females each. The control group received 0.5 ml/100 g of saline. Group I received 0.25 mg/kg, Groups II received 0.5 mg/kg and Group III received 1.0 mg/kg of CaRest-M3™. The route of

TABLE 20

CULTURE TIME IN HOURS (h) AND MICROFILARIAE (mf) MOVEMENT STATE

| Culture Fluid | Compound | Conc. (M) | 5' | 10' | 3 h | 5 h | 8 h | 21 h | 26 h | 45 h | 48 h | 69 h | 78 h | 104 h | 142 h | 174 h |
|---|---|---|---|---|---|---|---|---|---|---|---|---|---|---|---|---|
| DMEM | CaRest-M3 ™ | $10^{-2}$ | − | − | − | − | − | − | − | − | − | − | − | − | − | − |
| DMEM | CaRest-M3 ™ | $10^{-3}$ | ± | − | − | − | − | − | − | − | − | − | − | − | − | − |
| DMEM | CaRest-M3 ™ | $10^{-4}$ | < | < | << | − | − | − | − | − | − | − | − | − | − | − |
| DMEM | CaRest-M3 ™ | | + | + | + | + | + | + | + | + | + | + | + | + | + | + |

\+ Movement (all mf)
− No movement (all mf)
± Some move, some not move
< Decreased movement all mf

TABLE 21

CULTURE TIME IN HOURS (h) AND ADULT WORM MOVEMENT STATE

| Culture Fluid | Compound | Conc. (M) | 40' | 1 h | 2.5 h | 3 h | 5 h | 24 h | 48 h | 72 h |
|---|---|---|---|---|---|---|---|---|---|---|
| DMEM | CaRest-M3 ™ | 1 | − | − | − | − | − | − | − | − |
| DMEM | CaRest-M3 ™ | $10^{-1}$ | < | − | − | − | − | − | − | − |
| DMEM | CaRest-M3 ™ | $50 \times 10^{-4}$ | < | < | < | − | − | − | − | − |
| DMEM | Control | | + | + | + | + | + | + | + | + |

\+ Movement (all worms)
− No movement (all worms)
± Some move, some not move
< Decreased movement all worms

EXAMPLE 18

Subacute Toxicity Study in Rats

Initial Study: Initially, 48 Wistar rats (24 male, 24 female) underwent a 14-day dose ranging study, receiving 14 daily doses of CaRest-M3™ of 0.5 mg/kg, 1.5 mg/kg and 3.0 mg/kg. There were 12 rats in each dose group. Treatment was by daily intraperitoneal injection. The control group received 0.5 ml/100 g of saline by the same method. The purpose of the dose-ranging study was to determine the doses for the 42-day subacute toxicity study.

The results of the dose-ranging study were as follows:

1. The 0.5 mg/kg dose group showed no pathological symptoms or mortality.
2. The 1.5 mg/kg dose group showed no mortality. Several animals experienced intraperitoneal spasms 5 minutes after injection which regenerated after the 3rd hour. Autopsy revealed slight to moderately severe sterile inflammation with fibrinous exudation in the abdominal cavity.
3. Five rats in the 3.0 mg/kg dose group died during treatment. The animals showed peritoneal spasm, mild dyspnoea, and atonicity of the hind legs 1 minute after the first four treatments. The animals experienced weight loss. Autopsy showed a medium to high quantity of exudate and fibrin in the abdominal cavity, the organs were fibrinously interlaced and covered by fibrin.

administration was intraperitoneal injection, once daily for 42 consecutive days. The animals were continuously observed for one hour following each treatment, then twice daily. Observations and studies included: pulse and respiratory rates, body mass, urinalysis, complete blood count with differential, platelet count, prothrombin time, total bilirubin, SGOT, SGPT, alkaline phosphatase, creatinine phosphokinase and urea nitrogen. The animals were followed for 28 days after the last treatment, then all the animals had post-mortem and histopathological examinations.

Results

1. The 0.25 mg/kg dose caused no general toxic symptoms. One animal died during the treatment. The death was attributed to a "needle caused mechanical lesion" in the left renal area. Autopsy revealed mild fibrinous secretion in the abdominal cavity in some of the animals.
2. The 0.5 mg/kg dose caused no general toxic symptoms or mortality in the test animals. Autopsy revealed fibrinous exudate on the serous membrane of some of the abdominal organs. Hematological changes were registered due to local irritation.
3. The 1.0 mg/kg dose caused 4 deaths in the test animals. At autopsy, intensive fibrin secretion in the abdominal cavity was noted and attributed to local irritation. Hematological changes were seen as well. The toxicity and deaths were deemed secondary to severe local irritation.

Conclusion

CaRest-M3™ administered to rats intraperitoneally in doses of 0.25 and 0.5 mg/kg for 42 consecutive days produced no general toxic symptoms in the test animals. CaRest-M3™ administered to rats IP at a dose of 1.0 mg/kg for 42 days caused severe local irritation in the abdomen with fibrin deposition and intestinal obstruction in some of the animals.

EXAMPLE 19

Acute Toxicity Study of CaRest-M3™ in Dogs

Four male and four female beagle dogs were given the following one time doses of CaRest-M3™: 0.15 mg/kg, 0.3 mg/kg, 0.75 mg/kg, 1.2 mg/kg, 2.4 mg/kg, and 4.8 mg/kg. The route of administration was intravenous injection. This preliminary screening, a small scale acute toxicity study, established the doses to be used in the 30 day subacute toxicity study. No mortality was seen in any of the test groups.

The results of the preliminary study were as follows:
1. One time injection of CaRest-M3™ at a dose of 0.15 or 0.3 mg/kg caused no toxic symptoms, mortality, or local irritation in the animals.
2. One time injection of CaRest-M3™ at a dose of 0.75 or 1.2 mg/kg caused no pathological symptoms or mortality, however, reversible local irritation at the site of injection was observed in 50% of the test animals.
3. One time injection of CaRest-M3™ at a dose of 2.4 or 4.8 mg/kg caused catatony, salivation and dyspnoea as well as local irritation at the site of injection.

Materials & Methods

The doses used for the 30 day subacute toxicity study were 0.15, 0.45 and 0.75 mg/kg. Twenty-four dogs were divided into four groups, each with three male animals and three female animals. The control group received 0.5 ml/kg of saline. Group I received 0.15 mg/kg, Group II received 0.45 mg/kg and Group III received 0.75 mg/kg of CaRest-M3™. The route of administration was intravenous injection over 1–2 minutes, once daily for 30 consecutive days. The animals were continuously observed for one hour following each treatment, then twice daily. Observations and studies included: pulse and respiratory rates, body mass, urinalysis, complete blood count with differential, platelet count, prothrombin time, total bilirubin, SGOT, SGPT, alkaline phosphatase, creatinine phosphokinase, urea nitrogen, electrocardiogram, an ophthalmologic exam and an audiology exam. One day after the last treatment, all the animals were euthanized had post-mortem gross and histopathological examinations on major organ systems.

Results

1. The 0.15 mg/kg dose caused no general toxic symptoms or mortality in the test animals. Mild to moderate local irritation was observed at the site of injection by day 30. This was also seen in some of the control animals.
2. The 0.45 mg/kg dose caused no general toxic symptoms or mortality in the test animals. Local edema at the site of injection was seen, increasing in severity with the number of treatments.
3. The 0.75 mg/kg dose caused no general toxic symptoms or mortality in the test animals. Severe local irritation and edema was observed at the site of injection. Histologic examination of the injection site revealed congestive edema. Some of the animals' white blood count increased with the onset of the local irritation. The above dose of the test compound caused no other hematologic, blood chemical or histopathological change.

Conclusion

The latentiated alpha-ketoaldehyde, CaRest-M3™, administered to beagle dogs in doses of 0.15, 0.45 and 0.75 mg/kg for 30 consecutive days produced no general toxic symptoms or mortality in the test animals. Moderate to severe local irritation and edema was observed with the 0.45 and 0.75 mg/kg doses.

EXAMPLE 20

Acute Toxicity Study of CaRest-M3™ in Mice

Purpose: To assess the acute toxicity of CaRest-M3™ after a single intravenous or intraperitoneal injection and to determine the maximum tolerated dose of $LD_{50}$ of the test material.

Choice of Species: CD1 mice.

Choice of Route of Administration:

Intravenous—in accordance with anticipated clinical route of administration.

Intraperitoneal—to provide a guideline for in-vivo tumor model testing.

Test Material: CaRest-M3™

Test Animals: CD1 mice obtained from Charles River Breeding Laboratories, Wilmington, Mass.

Weight:
Males: 20±2 g
Females: 20±2 g

Housing: Animals were housed in plastic cages five to a cage. Room temperature was controlled to 18°–26° C. Humidity was controlled to 40–70%. Fluorescent lighting was controlled automatically to provide alternate light and day cycles of approximately 12 hours each. Pellets or rodent chow were available ad libitum. Tap water, untreated with additional chlorine, was provided by water bottles ad libitum.

Animal Health: Animals used in this study were examined by qualified personnel for their health status prior to the commencement of the study. Animals were allowed to adapt to their new surroundings for 3–7 days prior to the commencement of the study.

Acute Toxicity Study: After a dose ranging study was completed and the data was analyzed, an acute toxicity study was performed to determine maximum tolerated dose of $LD_{50}$ with single dose injection of CaRest-M3™.

Treatment: Animals were dosed intravenously at the following doses (Table 22).

TABLE 22

| | | | Number of Animals | |
|---|---|---|---|---|
| Group | Treatment | Dose (mg/kg) | M | F |
| 1 | Control | 0.2 ml NS | 4 | 4 |
| 2 | CaRest-M3 ™ | 20 | 10 | 10 |
| 3 | CaRest-M3 ™ | 26 | 10 | 10 |
| 4 | CaRest-M3 ™ | 32 | 10 | 10 |
| 5 | CaRest-M3 ™ | 38 | 10 | 10 |
| 6 | CaRest-M3 ™ | 44 | 10 | 10 |
| 7 | CaRest-M3 ™ | 50 | 10 | 10 |

The results of the intravenous injection toxicity study are shown in FIG. 5 and Table 23.

TABLE 23

ACUTE TOXICITY STUDY IN CD1 MICE - INTERVENOUS

| SEX | DOSE (mg/kg) | DAY 1 | 2 | 3 | 4 | 5 | 6 | 7 | 8 | 9 | 10 |
|---|---|---|---|---|---|---|---|---|---|---|---|
| SURVIVAL OF MALE MICE INJECTED INTRAVENOUSLY WITH CaRest-M3 | | | | | | | | | | | |
| M | Control | 10/10 | 10/10 | 10/10 | 10/10 | 10/10 | 10/10 | 10/10 | 10/10 | 10/10 | 10/10 |
| M | 20.0 | 10/10 | 10/10 | 10/10 | 10/10 | 10/10 | 10/10 | 10/10 | 10/10 | 10/10 | 10/10 |
| M | 26.0 | 10/10 | 10/10 | 10/10 | 10/10 | 10/10 | 10/10 | 10/10 | 10/10 | 10/10 | 10/10 |
| M | 32.0 | 10/10 | 10/10 | 10/10 | 10/10 | 10/10 | 10/10 | 10/10 | 10/10 | 10/10 | 10/10 |
| M | 38.0 | 9/10 | 9/10 | 9/10 | 9/10 | 9/10 | 9/10 | 9/10 | 9/10 | 9/10 | 9/10 |
| M | 44.0 | 7/10 | 7/10 | 7/10 | 7/10 | 7/10 | 7/10 | 7/10 | 7/10 | 7/10 | 7/10 |
| M | 50.0 | 6/10 | 3/10 | 1/10 | 1/10 | 1/10 | 1/10 | 10/1 | 1/10 | 1/10 | 1/10 |
| SURVIVAL OF FEMALE MICE INJECTED INTRAVENOUSLY WITH CaRest-M3 | | | | | | | | | | | |
| F | Control | 10/10 | 10/10 | 10/10 | 10/10 | 10/10 | 10/10 | 10/10 | 10/10 | 10/10 | 10/10 |
| F | 20.0 | 10/10 | 10/10 | 10/10 | 10/10 | 10/10 | 10/10 | 10/10 | 10/10 | 10/10 | 10/10 |
| F | 26.0 | 10/10 | 10/10 | 10/10 | 10/10 | 10/10 | 10/10 | 10/10 | 10/10 | 10/10 | 10/10 |
| F | 32.0 | 10/10 | 10/10 | 10/10 | 10/10 | 10/10 | 10/10 | 10/10 | 10/10 | 10/10 | 10/10 |
| F | 38.0 | 9/10 | 9/10 | 9/10 | 9/10 | 9/10 | 9/10 | 9/10 | 9/10 | 9/10 | 9/10 |
| F | 44.0 | 8/10 | 8/10 | 8/10 | 8/10 | 8/10 | 8/10 | 8/10 | 8/10 | 8/10 | 8/10 |
| F | 50.0 | 8/10 | 5/10 | 3/10 | 3/10 | 2/10 | 2/10 | 2/10 | 2/10 | 2/10 | 2/10 |

Treatment: Animals were dosed intraperitoneally at the following doses (Table 24). The initial dose was determined from a small scale dose ranging study.

TABLE 24

| Group | Treatment | Dose (mg/kg) | Number of Animals M | F |
|---|---|---|---|---|
| 1 | Control | 1 ml NS | 4 | 4 |
| 2 | CaRest-M3 ™ | 6 | 10 | 10 |

TABLE 24-continued

| Group | Treatment | Dose (mg/kg) | Number of Animals M | F |
|---|---|---|---|---|
| 3 | CaRest-M3 ™ | 12 | 10 | 10 |
| 4 | CaRest-M3 ™ | 18 | 10 | 10 |
| 5 | CaRest-M3 ™ | 24 | 10 | 10 |
| 6 | CaRest-M3 ™ | 30 | 10 | 10 |

Figure 6:
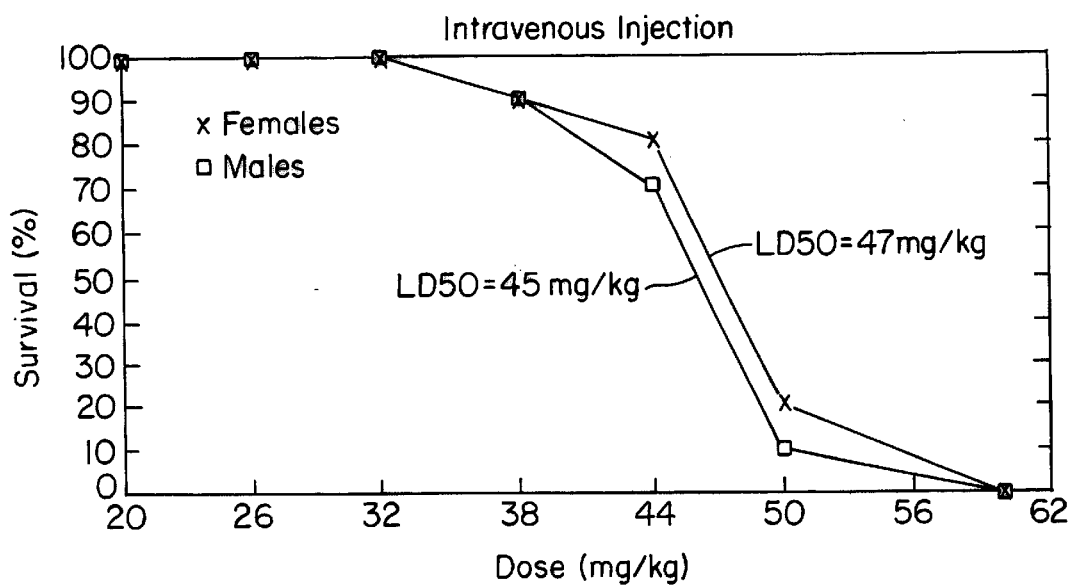
FIG. 6 is a graphic representation of the results of the acute toxicity study with CaRest-M3 in mice by intravenous injection.

The results of the intraperitoneal injection toxicity study are shown in FIG. 6 and Table 25.

Observations: Assessment of the animal's state and behavior after injection each hour for the first four hours followed by daily observation for 10 days. Body weight determination once per day for the first five days. Animal mortality with number dying each day. (see Tables 23 and 25).

TABLE 25

ACUTE TOXICITY STUDY IN CD1 MICE - INTRAPERITONEL

| SEX | DOSE (mg/kg) | DAY 1 | 2 | 3 | 4 | 5 | 6 | 7 | 8 | 9 | 10 |
|---|---|---|---|---|---|---|---|---|---|---|---|
| SURVIVAL OF MALE MICE INJECTED INTRAPERITONEALLY WITH CaRest-M3 | | | | | | | | | | | |
| M | Control | 10/10 | 10/10 | 10/10 | 10/10 | 10/10 | 10/10 | 10/10 | 10/10 | 10/10 | 10/10 |
| M | 6.0 | 10/10 | 10/10 | 10/10 | 10/10 | 10/10 | 10/10 | 10/10 | 10/10 | 10/10 | 10/10 |
| M | 12.0 | 10/10 | 10/10 | 10/10 | 10/10 | 10/10 | 10/10 | 10/10 | 10/10 | 10/10 | 10/10 |
| M | 18.0 | 10/10 | 10/10 | 10/10 | 10/10 | 10/10 | 10/10 | 10/10 | 10/10 | 10/10 | 10/10 |
| M | 24.0 | 8/10 | 8/10 | 8/10 | 8/10 | 8/10 | 8/10 | 8/10 | 8/10 | 8/10 | 8/10 |
| M | 30.0 | 0/10 | 0/10 | 0/10 | 0/10 | 0/10 | 0/10 | 0/10 | 0/10 | 0/10 | 0/10 |
| SURVIVAL OF FEMALE MICE INJECTED INTRAPERITONEALLY WITH CaRest-M3 | | | | | | | | | | | |
| F | Control | 10/10 | 10/10 | 10/10 | 10/10 | 10/10 | 10/10 | 10/10 | 10/10 | 10/10 | 10/10 |
| F | 18.0 | 10/10 | 10/10 | | | | | | | | |
| F | 24.0 | 9/10 | 7/10 | 6/10 | 6/10 | 6/10 | 6/10 | 5/10 | 5/10 | 5/10 | 5/10 |
| F | 30.0 | 0/10 | 0/10 | 0/10 | 0/10 | 0/10 | 0/10 | 0/10 | 0/10 | 0/10 | 0/10 |

TABLE 25-continued

ACUTE TOXICITY STUDY IN CD1 MICE - INTRAPERITONEL

| SEX | DOSE (mg/kg) | DAY | | | | | | | | | |
|---|---|---|---|---|---|---|---|---|---|---|---|
| | | 1 | 2 | 3 | 4 | 5 | 6 | 7 | 8 | 9 | 10 |
| F | 36.0 | 0/10 | 0/10 | 0/10 | 0/10 | 0/10 | 0/10 | 0/10 | 0/10 | 0/10 | 0/10 |
| F | 42.0 | 0/10 | 0/10 | 0/10 | 0/10 | 0/10 | 0/10 | 0/10 | 0/10 | 0/10 | 0/10 |

Equivalents

Those skilled in the art will recognize, or be able to ascertain using no more than routine experimentation, many equivalents to the specific embodiment of the invention described specifically herein. Such equivalents are intended to be encompassed in the scope of the following claims.

The invention claimed is:

1. A method of inhibiting tumor cell growth in a vertebrate host comprising administering to the vertebrate an effective amount of a chemically latentiated alpha-ketoaldehyde, wherein the tumor cell is selected from the group of tumors consisting of: melanomas, carcinomas and leukemias, and the carcinomas are from tissues selected from the group consisting of: lung, colon, kidney, ovary, brain, prostrate, and the chemically latentiated alpha-ketoaldehyde is selected from the group consisting of N-(1-hydroxyacetonyl) maleimide and acetylated N-(1-hydroxyacetonyl) maleimide.

2. The method of claim 1 wherein the acetylated N-1 (hydroxyacetonyl) maleimide is further modified to a structure having the formula:

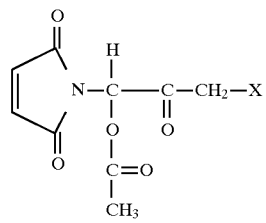

wherein X is selected from the group consisting of: —H; —OH; —CH=$CH_2$; —Cl; —$Cl_2$; —I; —Br; —$NH_2$; —NH—R; —N=$R_2$; and —R where R=($CH_{0-11}$—$CH_3$ or an aromatic or cyclic compound).

3. The method of claim 1 wherein the N-1 (hydroxyacetonyl) maleimide is further modified to a structure having the formula:

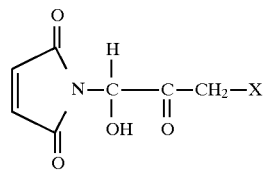

wherein X is selected from the group consisting of: —H; —OH; —CH=$CH_2$; —Cl; —$Cl_2$; —I; —Br; —$NH_2$; —NH—R; —N=$R_2$; and —R where R=($CH_{0-11}$—$CH_3$ or an aromatic or cyclic compound).

* * * * *